(12) United States Patent
Makinoshima et al.

(10) Patent No.: US 10,310,377 B2
(45) Date of Patent: *Jun. 4, 2019

(54) MATERIAL FOR FORMING FILM FOR LITHOGRAPHY, COMPOSITION FOR FORMING FILM FOR LITHOGRAPHY, FILM FOR LITHOGRAPHY, PATTERN FORMING METHOD AND PURIFICATION METHOD

(71) Applicant: Mitsubishi Gas Chemical Company, Inc., Tokyo (JP)

(72) Inventors: Takashi Makinoshima, Kanagawa (JP); Masatoshi Echigo, Kanagawa (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/309,758

(22) PCT Filed: May 8, 2015

(86) PCT No.: PCT/JP2015/063285
§ 371 (c)(1),
(2) Date: Nov. 8, 2016

(87) PCT Pub. No.: WO2015/170736
PCT Pub. Date: Nov. 12, 2015

(65) Prior Publication Data
US 2017/0144954 A1 May 25, 2017

(30) Foreign Application Priority Data
May 8, 2014 (JP) .................................. 2014-097000

(51) Int. Cl.
*G03F 7/004* (2006.01)
*G03F 7/30* (2006.01)
(Continued)

(52) U.S. Cl.
CPC .............. *G03F 7/039* (2013.01); *C07C 25/22* (2013.01); *C07C 39/12* (2013.01); *C07C 43/285* (2013.01); *C07C 69/52* (2013.01); *C07C 69/533* (2013.01); *C07C 205/06* (2013.01); *C07C 211/61* (2013.01); *C07C 321/26* (2013.01); *C07D 303/18* (2013.01); *C07D 303/36* (2013.01); *C08G 8/08* (2013.01); *C08G 8/12* (2013.01); *C08G 8/14* (2013.01); *C08G 8/16* (2013.01); *C08G 8/18* (2013.01); *C08G 8/24* (2013.01); *C08G 10/02* (2013.01); *C08G 12/02* (2013.01); *C08G 18/02* (2013.01); *C09D 161/06* (2013.01); *G03F 7/0045* (2013.01); *G03F 7/0392* (2013.01); *G03F 7/11* (2013.01); *G03F 7/162* (2013.01); *G03F 7/168* (2013.01); *G03F 7/2037* (2013.01); *G03F 7/26* (2013.01);
(Continued)

(58) Field of Classification Search
CPC ...... G03F 7/0045; G03F 7/0392; G03F 7/052; G03F 7/091; G03F 7/30; G03C 1/8155; C08G 8/12; C08G 8/14; C08G 8/16; C08G 8/18; C08G 8/24; C08G 10/02; C08G 12/02; C08G 18/02
USPC ..... 430/270.1, 326, 323, 512; 528/125, 129, 528/148, 149, 150, 151, 153, 155, 176, 528/196, 205, 211, 159
See application file for complete search history.

(56) References Cited

U.S. PATENT DOCUMENTS 3,640,718 A * 2/1972 Smith .................... G03C 1/675
430/270.1
4,725,422 A * 2/1988 Miyabayashi ........ C04B 35/524
264/29.1
(Continued)

FOREIGN PATENT DOCUMENTS

EP 3141959 A1 3/2017
JP 2002-231450 A 8/2002
(Continued)

OTHER PUBLICATIONS

International Search Report dated Jul. 14, 2015, for PCT/JP2015/063285 and English translation of the same (9 pages).
(Continued)

*Primary Examiner* — John S Chu
(74) *Attorney, Agent, or Firm* — Fitch, Even, Tabin & Flannery LLP

(57) ABSTRACT

The material for forming a film for lithography according to the present invention contains a compound represented by the following formula (1):

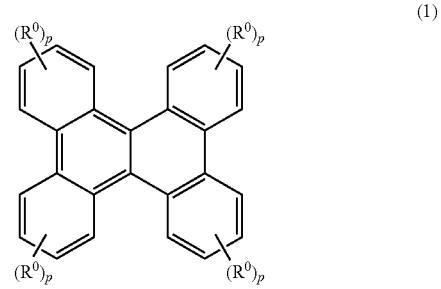

wherein, each $R^0$ independently represents a monovalent group having an oxygen atom, a monovalent group having a sulfur atom, a monovalent group having a nitrogen atom, a hydrocarbon group or a halogen atom, and each p is independently an integer of 0 to 4.

17 Claims, No Drawings

(51) Int. Cl.

| | | |
|---|---|---|
| C08G 8/12 | (2006.01) | |
| C08G 8/14 | (2006.01) | |
| C08G 8/18 | (2006.01) | |
| C08G 10/02 | (2006.01) | |
| C08G 12/02 | (2006.01) | |
| G03F 7/039 | (2006.01) | |
| C08G 18/02 | (2006.01) | |
| C08G 8/24 | (2006.01) | |
| C08G 8/16 | (2006.01) | |
| G03F 7/11 | (2006.01) | |
| G03F 7/26 | (2006.01) | |
| H01L 21/027 | (2006.01) | |
| C07C 25/22 | (2006.01) | |
| C07C 39/12 | (2006.01) | |
| C07C 43/285 | (2006.01) | |
| C07C 69/52 | (2006.01) | |
| C07C 69/533 | (2006.01) | |
| C07C 205/06 | (2006.01) | |
| C07C 211/61 | (2006.01) | |
| C07C 321/26 | (2006.01) | |
| C07D 303/18 | (2006.01) | |
| C07D 303/36 | (2006.01) | |
| C08G 8/08 | (2006.01) | |
| C09D 161/06 | (2006.01) | |
| G03F 7/16 | (2006.01) | |
| G03F 7/20 | (2006.01) | |
| G03F 7/32 | (2006.01) | |
| G03F 7/38 | (2006.01) | |
| H01L 21/306 | (2006.01) | |
| H01L 21/308 | (2006.01) | |
| G03C 1/815 | (2006.01) | |

(52) U.S. Cl.
CPC ............... *G03F 7/322* (2013.01); *G03F 7/38* (2013.01); *H01L 21/027* (2013.01); *H01L 21/3081* (2013.01); *H01L 21/3086* (2013.01); *H01L 21/30604* (2013.01); *C07C 2603/54* (2017.05); *G03C 1/8155* (2013.01)

(56) References Cited

U.S. PATENT DOCUMENTS 6,416,887 B1* 7/2002 Tokito ............... C07C 211/61
313/504

| 2004/0106004 | A1* | 6/2004 | Li ................... C07C 211/61 428/690 |
| 2005/0255712 | A1 | 11/2005 | Kato et al. |
| 2008/0153031 | A1 | 6/2008 | Echigo et al. |
| 2009/0163693 | A1 | 6/2009 | Kim |
| 2010/0316950 | A1 | 12/2010 | Oguro et al. |
| 2012/0171611 | A1 | 7/2012 | Ideno et al. |

FOREIGN PATENT DOCUMENTS

| JP | 2002/334869 A | 11/2002 |
|---|---|---|
| JP | 2004-177668 A | 6/2004 |
| JP | 2004-271838 A | 9/2004 |
| JP | 2005-250434 A | 9/2005 |
| JP | 2005-321587 A | 11/2005 |
| JP | 2005/326838 A | 11/2005 |
| JP | 2006-162858 A | 6/2006 |
| JP | 2006-178083 A | 7/2006 |
| JP | 2007-226170 A | 9/2007 |
| JP | 2007-226204 A | 9/2007 |
| JP | 2008-145539 A | 6/2008 |
| JP | 2009-511732 A | 3/2009 |
| JP | 2009-173623 A | 8/2009 |
| JP | 2013-227307 A | 11/2013 |
| JP | 2013227307 * | 11/2013 |
| JP | 2014-152164 A | 8/2014 |
| WO | 2004/066377 A1 | 8/2004 |
| WO | 2008/004751 A1 | 1/2008 |
| WO | 2009/072465 A1 | 6/2009 |
| WO | 2011-034062 A1 | 3/2011 |

OTHER PUBLICATIONS

Patent Cooperation Treaty, International Search Report for International Application No. PCT/JP2015/063272 dated Jun. 2, 2015 and English translation (5 pages).

Patent Cooperation Treaty, Written Opinion of the International Searching Authority for International Application No. PCT/JP2015/063272 dated Jun. 2, 2015 and English translation (7 pages).

Nakayama Tomonari, Nomura Masayoshi, Haga Kohji, and Ueda Mitsuru, "A New Three-Component Photoresist Based Calix[4]resorcinarene Derivative, a Cross-linker, and a Photo-acid Generator," Bulletin of the Chemical Society of Japan, 1998, vol. 71, No. 12, pp. 2979-2984.

* cited by examiner

MATERIAL FOR FORMING FILM FOR LITHOGRAPHY, COMPOSITION FOR FORMING FILM FOR LITHOGRAPHY, FILM FOR LITHOGRAPHY, PATTERN FORMING METHOD AND PURIFICATION METHOD

CROSS-REFERENCE TO RELATED APPLICATIONS

This application is a U.S. national phase application filed under 35 U.S.C. § 371 of International Application PCT/JP2015/063285, filed on May 8, 2015, designating the United States, which claims priority from Japanese Application Number 2014-097000, filed May 8, 2014, which are hereby incorporated herein by reference in their entirety.

FIELD OF THE INVENTION

The present invention relates to a material for forming a film for lithography, containing a compound or a resin of a specified structure, a composition for forming a film for lithography, including the material, a film for lithography, formed using the composition, a photoresist pattern forming method using the composition, and a purification method of the material.

BACKGROUND OF THE INVENTION

Semiconductor devices are manufactured through microfabrication by lithography using a photoresist material, but are required to be made finer by a pattern rule in accordance with the increase in integration degree and the increase in speed of LSI in recent years. In lithography using exposure to light, which is currently used as a general-purpose technique, the resolution is now approaching the intrinsic limitation associated with the wavelength of the light source.

A light source for lithography, for use in forming a resist pattern, has a shorter wavelength from a KrF excimer laser (248 nm) to an ArF excimer laser (193 nm). However, as the resist pattern is made finer and finer, there arise a problem of resolution and a problem of collapse of the resist pattern after development, and therefore there is demanded for making a resist film thinner. If the resist film is merely made thinner in response to such a demand, it is difficult to achieve the resist pattern having a film thickness sufficient for processing a substrate. Accordingly, there is increasingly required a process in which not only the resist pattern but also a resist underlayer film is prepared between a resist and a semiconductor substrate to be processed and the resist underlayer film is allowed to have a function as a mask at the time of processing the substrate.

Currently, as the resist underlayer film for such a process, various ones are known. Examples can include a resist underlayer film for lithography, having a selection ratio of dry etching rate close to the resist, unlike a conventional resist underlayer film having a high etching rate. As the material for forming such a resist underlayer film for lithography, there has been proposed a material for forming an underlayer film for multilayer resist process, containing a resin component having at least a substituent which releases a terminal group to form a sulfonic acid residue when a predetermined energy is applied, and a solvent (see, for example, Patent Literature 1). In addition, examples can include a resist underlayer film for lithography, having a smaller selection ratio of dry etching rate than the resist. As the material for forming such a resist underlayer film for lithography, there has been proposed a resist underlayer film material including a polymer having a specified repeating unit (see, for example, Patent Literature 2). Furthermore, examples can include a resist underlayer film for lithography, having a smaller selection ratio of dry etching rate than the semiconductor substrate. As the material for forming such a resist underlayer film for lithography, there has been proposed a resist underlayer film material including a polymer formed by co-polymerizing a repeating unit of acenaphthylene, and a substituted or non-substituted repeating unit having a hydroxy group (see, for example, Patent Literature 3).

On the other hand, as a material for allowing such a resist underlayer film to have a high etching resistance, an amorphous carbon underlayer film is well known, which is formed by CVD using methane gas, ethane gas, acetylene gas, or the like as a raw material.

In addition, as a material that is excellent in optical characteristics and etching resistance and that is capable of being dissolved in a solvent and being applied to a wet process, the present inventors have proposed a composition for forming an underlayer film for lithography, which contains a naphthalene formaldehyde polymer including a specified constituent unit, and an organic solvent (see, for example, Patent Literatures 4 and 5).

Meanwhile, with respect to a forming method of an intermediate layer for use in forming a resist underlayer film in a three-layer process, for example, known are a forming method of a silicon nitride film (see, for example, Patent Literature 6), and a CVD forming method of a silicon nitride film (see, for example, Patent Literature 7). In addition, as an intermediate layer material for a three-layer process, known is a material containing a silsesquioxane-based silicon compound (see, for example, Patent Literatures 8 and 9).

CITATION LIST

Patent Literature

Patent Literature 1: Japanese Patent Laid-Open No. 2004-177668
Patent Literature 2: Japanese Patent Laid-Open No. 2004-271838
Patent Literature 3: Japanese Patent Laid-Open No. 2005-250434
Patent Literature 4: International Publication No. WO 2009/072465
Patent Literature 5: International Publication No. WO 2011/034062
Patent Literature 6: Japanese Patent Laid-Open No. 2002-334869
Patent Literature 7: International Publication No. WO 2004/066377
Patent Literature 8: Japanese Patent Laid-Open No. 2007-226170
Patent Literature 9: Japanese Patent Laid-Open No. 2007-226204

SUMMARY OF INVENTION

As described above, many materials for forming an underlayer film for lithography have been conventionally proposed, but there are no ones that not only have such a high solvent solubility as to be able to be applied to a wet process such as a spin coating method or screen printing, but also simultaneously satisfy heat resistance and etching resistance at a high level, and thus a new material is required to be developed.

The present invention has been made in view of the above problem, and an object thereof is to provide a material for forming a film for lithography, which can be applied to a wet process and which can form a film for lithography, having a good etching resistance, a composition for forming a film for lithography, containing the material, and a pattern forming method using the composition.

The present inventors have intensively studied to solve the above problem, and as a result, have found that the above problem can be solved by using a compound or a resin having a specified structure, thereby leading to the completion of the present invention. That is, the present invention is as follows.

[1]

A material for forming a film for lithography, comprising a compound represented by the following formula (1):

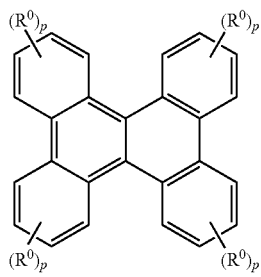
(1)

wherein, each $R^0$ independently represents a monovalent group having an oxygen atom, a monovalent group having a sulfur atom, a monovalent group having a nitrogen atom, a hydrocarbon group or a halogen atom, and each p is independently an integer of 0 to 4.

[2]

The material for forming the film for lithography according to [1], wherein at least one p is an integer of 1 to 4.

[3]

The material for forming the film for lithography according to [1] or [2], wherein at least one $R^0$ represents the monovalent group having the oxygen atom.

[4]

The material for forming the film for lithography according to [1], wherein the compound represented by the formula (1) is a compound represented by the following formula (2):

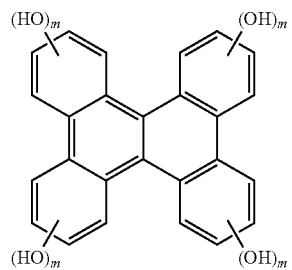
(2)

wherein, each m is independently an integer of 0 to 4, in which at least one m is an integer of 1 to 4.

[5]

The material for forming the film for lithography according to [4], wherein the compound represented by the formula (2) is at least one selected from the group consisting of compounds represented by the following formulae (2-1) to (2-6):

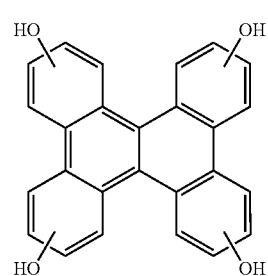
(2-1)

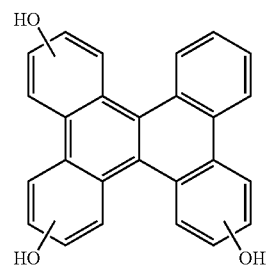
(2-2)

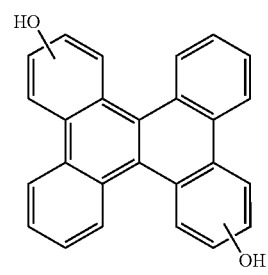
(2-3)

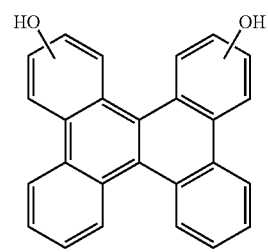
(2-4)

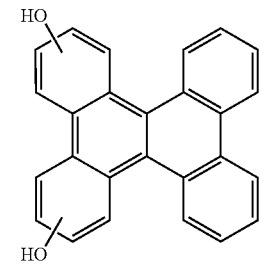
(2-5)

-continued (2-6)

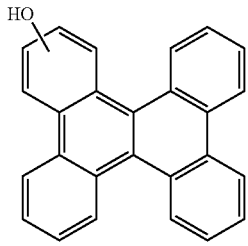

(2)

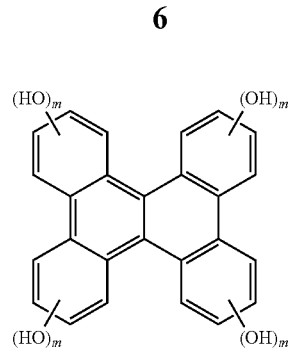

wherein, each m is independently an integer of 0 to 4, in which at least one m is an integer of 1 to 4.

[12]
The resin according to any of [6] to [11], having at least one structure selected from the group consisting of structures represented by the following formulae (3-1) to (3-16):

[6]
A resin obtained through a reaction of at least a compound represented by the following formula (1) with a compound having crosslinking reactivity:

(1)

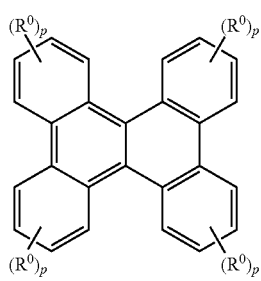

wherein, each $R^0$ independently represents a monovalent group having an oxygen atom, a monovalent group having a sulfur atom, a monovalent group having a nitrogen atom, a hydrocarbon group or a halogen atom, and each p is independently an integer of 0 to 4.

[7]
The resin according to [6], wherein at least one p is an integer of 1 to 4.

[8]
The resin according to [6] or [7], wherein at least one $R^0$ represents the monovalent group having the oxygen atom.

[9]
The resin according to any of [6] to [8], wherein the compound having crosslinking reactivity is an aldehyde, a ketone, a carboxylic acid, a carboxylic acid halide, a halogen-containing compound, an amino compound, an imino compound, an isocyanate, or an unsaturated hydrocarbon group-containing compound.

[10]
The resin according to any of [6] to [9], which is at least one selected from the group consisting of a novolac-based resin, an aralkyl-based resin, a hydroxystyrene-based resin, a (meth)acrylic acid-based resin and copolymers thereof.

[11]
The resin according to any of [6] to [10], wherein the compound represented by the formula (1) is a compound represented by the following formula (2):

(3-1)

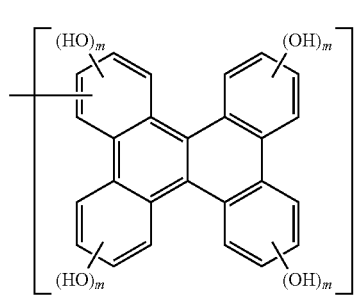

(3-2)

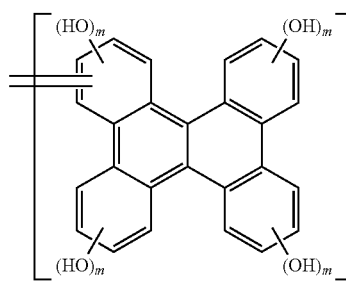

(3-3)

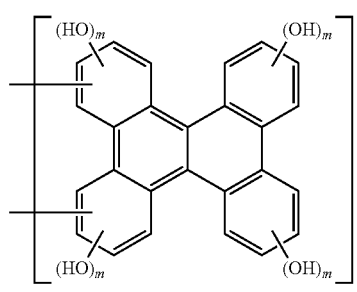

(3-4)

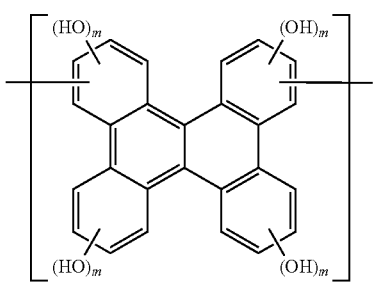

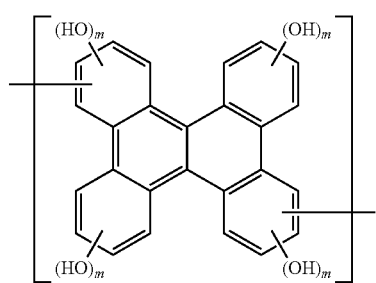
(3-5)
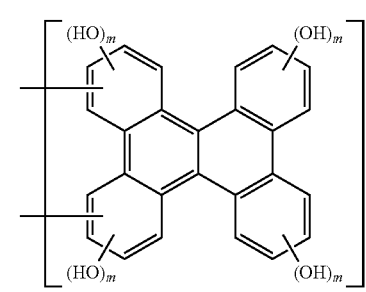
(3-6)
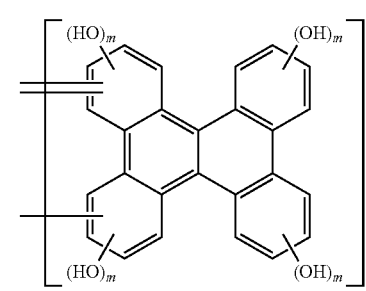
(3-7)
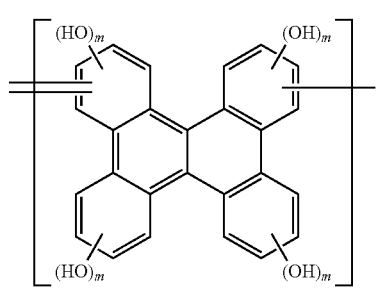
(3-8)
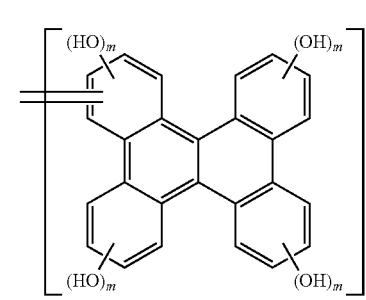
(3-9)
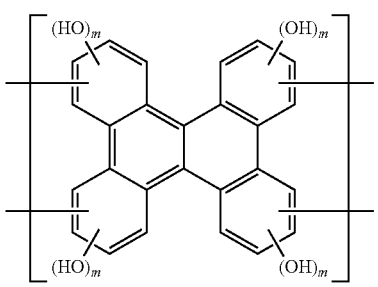
(3-10)
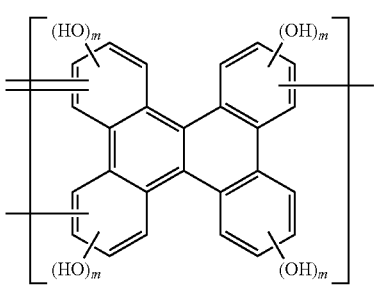
(3-11)
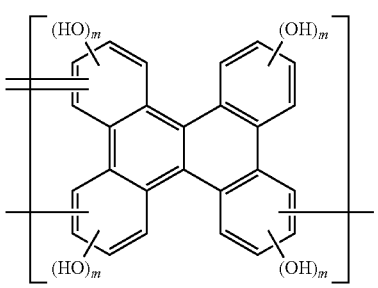
(3-12)
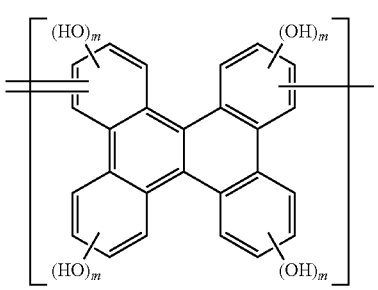
(3-13)
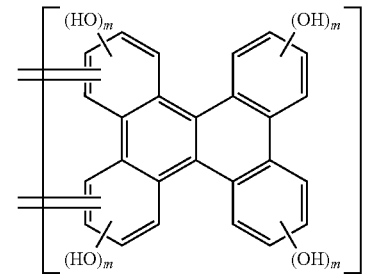
(3-14)

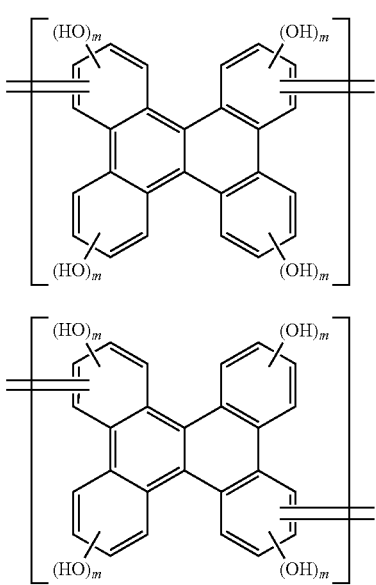

(3-15)

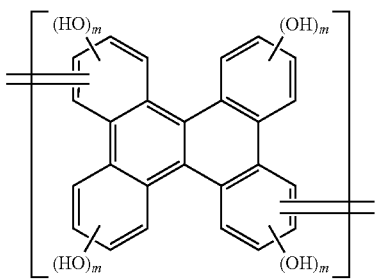

(3-16)

wherein, each m is independently an integer of 0 to 4, in which at least one m is an integer of 1 to 4.

[13]

A material for forming a film for lithography, comprising the resin according to any of [6] to [12].

[14]

A composition for forming a film for lithography, comprising the material for forming the film for lithography according to any of [1] to [5] and/or the material for forming the film for lithography according to [13], and an organic solvent.

[15]

The composition for forming the film for lithography according to [14], further comprising an acid generating agent.

[16]

The composition for forming the film for lithography according to [14] or [15], further comprising a crosslinking agent.

[17]

A film for lithography, formed using the composition for forming the film for lithography according to any of [14] to [16].

[18]

A resist pattern forming method, comprising step (A-1) of forming a film on a substrate by using the composition for forming the film for lithography according to any of [14] to [16], step (A-2) of forming at least one photoresist layer on the film, and step (A-3) of, after step (A-2), irradiating a predetermined region of the photoresist layer with radiation, followed by developing.

[19]

A circuit pattern forming method comprising step (B-1) of forming a film on a substrate by using the composition for forming the film for lithography according to any of [14] to [16], step (B-2) of forming an intermediate layer film on the film by using a silicon atom-containing resist intermediate layer film material, step (B-3) of forming at least one photoresist layer on the intermediate layer film, step (B-4) of, after step (B-3), irradiating a predetermined region of the photoresist layer with radiation, followed by developing to form a resist pattern, and step (B-5) of, after step (B-4), etching the intermediate layer film with the resist pattern as a mask, etching the film with the obtained intermediate layer film pattern as an etching mask and etching the substrate with the obtained film pattern as an etching mask, to form a pattern on the substrate.

[20]

A method for purifying the material for forming the film for lithography according to any of [1] to [5] and [13], the method comprising a step of bringing a solution (A) comprising an organic solvent optionally immiscible with water, and the material for forming a film for lithography into contact with an acidic aqueous solution for extraction.

The material for forming a film for lithography of the present invention can be applied to a wet process and can form a film for lithography, having a good etching resistance.

DESCRIPTION OF EMBODIMENTS

Hereinafter, an embodiment (hereinafter, referred to as "the present embodiment") of the present invention will be described. It is to be noted that the present embodiments are illustrative for describing the present invention, and the present invention is not limited only to the present embodiments.

[Film for Lithography]

A film for lithography exhibits good absorbency of light at a wavelength for use in manufacturing of a semiconductor device, therefore has a high effect of preventing reflection light, and also has a high dry etching rate as compared with a photoresist layer. Examples of an application of such a film for lithography include, but are not limited to the following, an antireflective film; a film for planarization that is embedded in the step of a layer to be processed; a resist upperlayer film that is not intermixed with a resist and particularly shields, for example, light at a long wavelength for use in exposure, in which the light is not preferable in exposure with extreme ultraviolet rays to allow for selective penetration of only extreme ultraviolet rays, and that can be developed by a developer after exposure; and a resist underlayer film that has high dry etching rate and heat resistance as compared with a photoresist layer.

[Material for Forming Film for Lithography]

A material for forming a film for lithography of the present embodiment comprises a compound represented by the following formula (1).

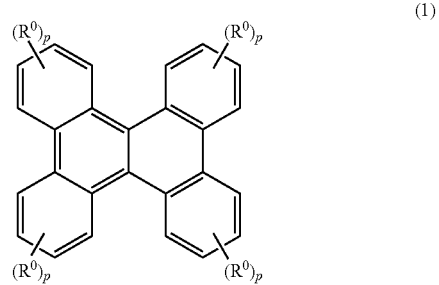

(1)

In the formula (1), each $R^0$ independently represents a monovalent group having an oxygen atom, a monovalent group having a sulfur atom, a monovalent group having a nitrogen atom, a hydrocarbon group or a halogen atom. Each p is independently an integer of 0 to 4.

The material for forming a film for lithography of the present embodiment has such a configuration, and therefore can be applied to a wet process and can form a film for lithography, having a good etching resistance. Furthermore, the material for forming a film for lithography of the present embodiment is excellent in heat resistance and etching resistance. In particular, the material for forming a film for lithography of the present embodiment can form a film which has a high heat resistance due to a polycyclic aromatic structure (dibenzo[g,p]chrysene backbone), whose degradation is suppressed at high-temperature baking, and which is also excellent in etching resistance to oxygen plasma etching or the like. Furthermore, the material for forming a film for lithography of the present embodiment has a high solubility in an organic solvent, has a high solubility in a safe solvent and has a good product quality stability, regardless of having a polycyclic aromatic structure. Additionally, the material for forming a film for lithography of the present embodiment is also excellent in adhesiveness with a resist layer and a resist intermediate layer film material, and therefore can provide an excellent resist pattern. As described above, the material for forming a film for lithography of the present embodiment is preferably used in formation of a film for lithography for various applications recited above, and in particular, more preferably used in an application of an underlayer film for lithography.

Herein, examples of the monovalent group containing an oxygen atom include, but not limited to, an acyl group having 1 to 20 carbon atoms, an alkoxycarbonyl group having 2 to 20 carbon atoms, a linear alkyloxy group having 1 to 6 carbon atoms, a branched alkyloxy group having 3 to 20 carbon atoms, a cyclic alkyloxy group having 3 to 20 carbon atoms, a linear alkenyloxy group having 2 to 6 carbon atoms, a branched alkenyloxy group having 3 to 6 carbon atoms, a cyclic alkenyloxy group having 3 to 10 carbon atoms, an aryloxy group having 6 to 10 carbon atoms, an acyloxy group having 1 to 20 carbon atoms, an alkoxycarbonyloxy group having 2 to 20 carbon atoms, an alkoxycarbonylalkyl group having 2 to 20 carbon atoms, a 1-substituted alkoxymethyl group having 2 to 20 carbon atoms, a cyclic ether oxy group having 2 to 20 carbon atoms, an alkoxyalkyloxy group having 2 to 20 carbon atoms, a glycidyloxy group, an allyloxy group, a (meth)acryl group, a glycidyl acrylate group, a glycidyl methacrylate group, and a hydroxyl group.

Examples of the acyl group having 1 to 20 carbon atoms include, but not limited to, a methanoyl group (formyl group), an ethanoyl group (acetyl group), a propanoyl group, a butanoyl group, a pentanoyl group, a hexanoyl group, an octanoyl group, a decanoyl group, and a benzoyl group.

Examples of the alkoxycarbonyl group having 2 to 20 carbon atoms include, but not limited to, a methoxycarbonyl group, an ethoxycarbonyl group, a propoxycarbonyl group, a butoxycarbonyl group, a pentyloxycarbonyl group, a hexyloxycarbonyl group, an octyloxycarbonyl group, and a decyloxycarbonyl group.

Examples of the linear alkyloxy group having 1 to 6 carbon atoms include, but not limited to, a methoxy group, an ethoxy group, a n-propoxy group, a n-butoxy group, a n-pentyloxy group, and a n-hexyloxy group.

Examples of the branched alkyloxy group having 3 to 20 carbon atoms include, but not limited to, an isopropoxy group, an isobutoxy group, and a tert-butoxy group.

Examples of the cyclic alkyloxy group having 3 to 20 carbon atoms include, but not limited to, a cyclopropoxy group, a cyclobutoxy group, a cyclopentyloxy group, a cyclohexyloxy group, a cyclooctyloxy group, and a cyclodecyloxy group.

Examples of the linear alkenyloxy group having 2 to 6 carbon atoms include, but not limited to, a vinyloxy group, a 1-propenyloxy group, a 2-propenyloxy group, a 1-butenyloxy group, and a 2-butenyloxy group.

Examples of the branched alkenyloxy group having 3 to 6 carbon atoms include, but not limited to, an isopropenyloxy group, an isobutenyloxy group, an isopentenyloxy group, and an isohexenyloxy group.

Examples of the cyclic alkenyloxy group having 3 to 10 carbon atoms include, but not limited to, a cyclopropenyloxy group, a cyclobutenyloxy group, a cyclopentenyloxy group, a cyclohexenyloxy group, a cyclooctenyloxy group, and a cyclodecenyloxy group.

Examples of the aryloxy group having 6 to 10 carbon atoms include, but not limited to, a phenyloxy group (phenoxy group), a 1-naphthyloxy group, and a 2-naphthyloxy group.

Examples of the acyloxy group having 1 to 20 carbon atoms include, but not limited to, a formyloxy group, an acetyloxy group, a propionyloxy group, a butyryloxy group, an isobutyryloxy group, and a benzoyloxy group.

Examples of the alkoxycarbonyloxy group having 2 to 20 carbon atoms include, but not limited to, a methoxycarbonyloxy group, an ethoxycarbonyloxy group, a propoxycarbonyloxy group, a butoxycarbonyloxy group, an octyloxycarbonyloxy group, and a decyloxycarbonyloxy group.

Examples of the alkoxycarbonylalkyl group having 2 to 20 carbon atoms include, but not limited to, a methoxycarbonylmethyl group, an ethoxycarbonylmethyl group, a n-propoxycarbonylmethyl group, an isopropoxycarbonylmethyl group, and a n-butoxycarbonylmethyl group.

Examples of the 1-substituted alkoxymethyl group having 2 to 20 carbon atoms include, but not limited to, a 1-cyclopentylmethoxymethyl group, a 1-cyclopentylethoxymethyl group, a 1-cyclohexylmethoxymethyl group, a 1-cyclohexylethoxymethyl group, a 1-cyclooctylmethoxymethyl group, and a 1-adamantylmethoxymethyl group.

Examples of the cyclic ether oxy group having 2 to 20 carbon atoms include, but not limited to, a tetrahydropyranyloxy group, a tetrahydrofuranyloxy group, a tetrahydrothiopyranyloxy group, a tetrahydrothiofuranyloxy group, a 4-methoxytetrahydropyranyloxy group, and a 4-methoxytetrahydrothiopyranyloxy group.

Examples of the alkoxyalkyloxy group having 2 to 20 carbon atoms include, but not limited to, a methoxymethoxy group, an ethoxyethoxy group, a cyclohexyloxymethoxy group, a cyclohexyloxyethoxy group, a phenoxymethoxy group, and a phenoxyethoxy group.

Examples of the (meth)acryl group include, but not limited to, an acryloyloxy group and a methacryloyloxy group. The glycidyl acrylate group is not particularly limited as long as the glycidyl acrylate group can be obtained through the reaction of acrylic acid with a glycidyloxy group. Examples thereof include substituents in compounds shown in Synthesis Example 11 in Examples mentioned later. The glycidyl methacrylate group is not particularly limited as long as the glycidyl methacrylate group can be obtained through the reaction of methacrylic acid with a glycidyloxy group. Examples thereof include substituents in compounds shown in Synthesis Example 12 in Examples mentioned later.

Examples of the monovalent group containing a sulfur atom include, but not limited to, a thiol group. The monovalent group containing a sulfur atom is preferably a group in which the sulfur atom is directly bonded to a carbon atom constituting the dibenzo[g,p]chrysene skeleton.

Examples of the monovalent group containing a nitrogen atom include, but not limited to, a nitro group, an amino group, and a diazo group. The amino group may be an amino group in which one or two hydrogen atoms are substituted, and examples thereof include, but are not limited to the following, an amino group in which one or two hydrogen atoms are substituted with one or two glycidyl groups. The monovalent group containing a nitrogen atom is preferably a group in which the nitrogen atom is directly bonded to a carbon atom constituting the dibenzo[g,p]chrysene skeleton.

Examples of the hydrocarbon group include, but not limited to, a linear alkyl group having 1 to 6 carbon atoms, a branched alkyl group having 3 to 6 carbon atoms, a cyclic alkyl group having 3 to 10 carbon atoms, a linear alkenyl group having 2 to 6 carbon atoms, a branched alkenyl group having 3 to 6 carbon atoms, a cyclic alkenyl group having 3 to 10 carbon atoms, and an aryl group having 6 to 10 carbon atoms.

Examples of the linear alkyl group having 1 to 6 carbon atoms include, but not limited to, a methyl group, an ethyl group, a n-propyl group, a n-butyl group, a n-pentyl group, and a n-hexyl group.

Examples of the branched alkyl group having 3 to 6 carbon atoms include, but not limited to, an isopropyl group, an isobutyl group, a tert-butyl group, a neopentyl group, and a 2-hexyl group.

Examples of the cyclic alkyl group having 3 to 10 carbon atoms include, but not limited to, a cyclopropyl group, a cyclobutyl group, a cyclopentyl group, a cyclohexyl group, a cyclooctyl group, and a cyclodecyl group.

Examples of the linear alkenyl group having 2 to 6 carbon atoms include, but not limited to, a vinyl group, a 1-propenyl group, a 2-propenyl group (allyl group), a 1-butenyl group, a 2-butenyl group, a 2-pentenyl group, and a 2-hexenyl group.

Examples of the branched alkenyl group having 3 to 6 carbon atoms include, but not limited to, an isopropenyl group, an isobutenyl group, an isopentenyl group, and an isohexenyl group.

Examples of the cyclic alkenyl group having 3 to 10 carbon atoms include, but not limited to, a cyclopropenyl group, a cyclobutenyl group, a cyclopentenyl group, a cyclohexenyl group, a cyclohexenyl group, a cyclooctenyl group, and a cyclodecenyl group.

Examples of the aryl group having 6 to 10 carbon atoms include, but not limited to, a phenyl group and a naphthyl group.

Examples of the halogen atom include, but not limited to, a fluorine atom, a chlorine atom, a bromine atom, and an iodine atom.

In the present embodiment, at least one of p in the above formula (1) is preferably an integer of 1 to 4 from the viewpoint of solubility in a solvent.

In the present embodiment, at least one of $R^0$ in the above formula (1) is preferably a monovalent group containing an oxygen atom from the viewpoint of solubility in a solvent and imparting of crosslinkability.

Herein, the compound represented by the formula (1) is preferably a compound represented by the following formula (2) from the viewpoint that both of a high heat resistance and a high solubility are satisfied.

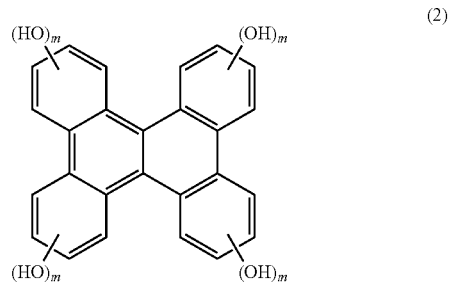

(2)

In the formula (2), each m is independently an integer of 0 to 4, in which at least one m is an integer of 1 to 4.

The compound represented by the formula (2) has a high heat resistance due to rigidity of its structure, while having a relatively low molecular weight, and therefore it can be used even in a high-temperature baking condition. In addition, the compound has a relatively low molecular weight and a low viscosity, and therefore, even when being applied to a substrate having a step (in particular, fine space, hole pattern and the like), it can be easily filled uniformly in every part of the step. Moreover, the coating film of the compound is excellent in smoothness, and as a result, a material for forming a film for lithography using the compound tends to be improved in terms of embedding properties in a relatively advantageous manner. Furthermore, the compound has a relatively high carbon concentration to thereby impart also a high etching resistance.

Herein, the compound represented by the formula (2) is preferably a compound represented by the following formulae (2-1) to (2-6) in terms of curability.

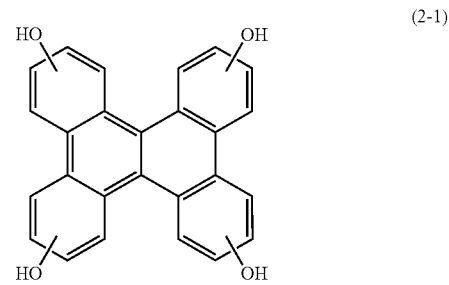

(2-1)

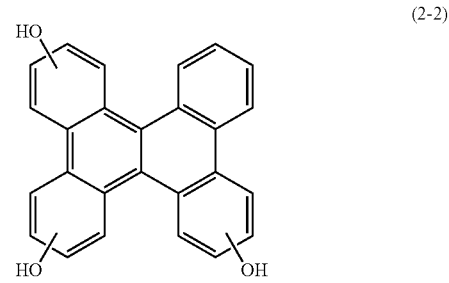

(2-2)

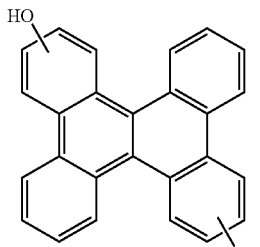

(2-3)

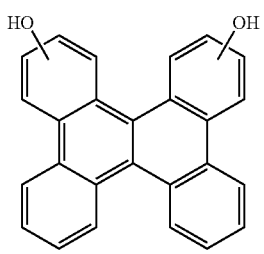

(2-4)

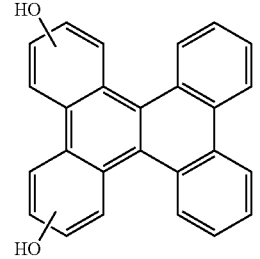

(2-5)

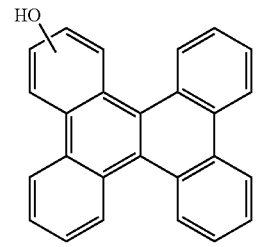

(2-6)

The compound represented by the formula (1) can be produced by a known method. Examples of the method include, but are not limited to the following, a method described in Japanese Patent Laid-Open No. 2013-227307. Alternatively, for example, the compound represented by the formula (2) can be obtained by sulfonating dibenzo[g,p]chrysene and then hydroxylating the resulting dibenzo[g,p]chrysene sulfonate. The compound can also be obtained by diazotizing an amino group of aminodibenzo[g,p]chrysene to provide a diazonium salt and then decomposing the resulting diazonium salt.

The compound represented by the formula (2) may be if necessary purified in order to enhance purity and reduce the amount of the remaining metal. When an acid catalyst and a co-catalyst remain, storage stability of a composition for forming an underlayer film generally tends to be deteriorated, and when a basic catalyst remains, sensitivity of a composition for forming an underlayer film generally tends to be deteriorated, and therefore purification for the purpose of reductions in the amounts of these catalysts may be performed.

Such purification can be performed by a known method as long as the compound represented by the formula (2) is not modified, and examples include, but are not particularly limited, a method of washing with water, a method of washing with an acidic aqueous solution, a method of washing with a basic aqueous solution, a method of treating with an ion exchange resin, and a method of treating with silica gel column chromatography. These purification methods are preferably performed in combinations of two or more. The method of washing with an acidic aqueous solution will be described later in detail.

The acidic aqueous solution, the basic aqueous solution, the ion exchange resin and the silica gel column chromatography can be appropriately selected optimally depending on the metal to be removed, the amount(s) and the type(s) of an acidic compound and/or a basic compound, the type of the compound represented by the formula (2), to be purified, and the like. Specifically, examples of the acidic aqueous solution include an aqueous solution of hydrochloric acid, nitric acid or acetic acid, having a concentration of 0.01 to 10 mol/L, examples of the basic aqueous solution include an aqueous ammonia solution having a concentration of 0.01 to 10 mol/L, and examples of the ion exchange resin include a cation exchange resin (for example, Amberlyst 15J-HG Dry produced by Organo Corporation), respectively.

Drying may also be performed after such purification. Such drying can be performed by a known method, and examples thereof include, but are not particularly limited, a vacuum drying method or a hot air drying method in a condition where the compound represented by the formula (2) is not modified.

In addition, the material for forming a film for lithography of the present embodiment includes a resin obtained through reacting at least the compound represented by the formula (1) with a compound having crosslinking reactivity.

The compound having crosslinking reactivity is not particularly limited as long as it can provide an oligomer or a polymer of the compound represented by the formula (1), and known one can be used therefor. Specific examples thereof include, but are not limited to the following, aldehyde, ketone, carboxylic acid, carboxylic halide, a halogen-containing compound, an amino compound, an imino compound, isocyanate, and an unsaturated hydrocarbon group-containing compound.

The resin is preferably at least one selected from the group consisting of a novolac-based resin, an aralkyl-based resin, a hydroxystyrene-based resin, a (meth)acrylic acid-based resin and copolymers thereof, from the viewpoint that both of a high heat resistance and a high solubility are satisfied.

The resin is preferably a resin obtained through reacting the compound represented by the formula (2) with a compound having crosslinking reactivity, from the viewpoint of ease of industrial production.

In addition, the resin preferably has at least one structure selected from the group consisting of structures represented by the formulae (3-1) to (3-16), from the viewpoint that both of a high heat resistance and a high solubility are satisfied.

(3-1)

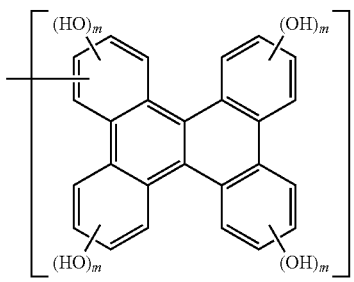

-continued
(3-2)
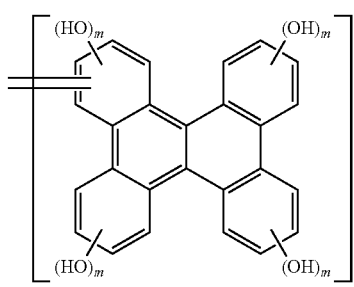
(3-7)
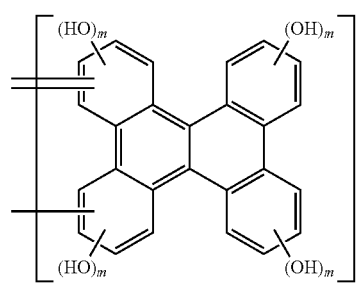
(3-3)
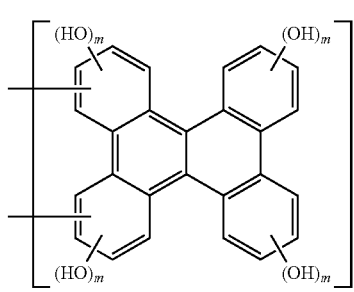
(3-8)
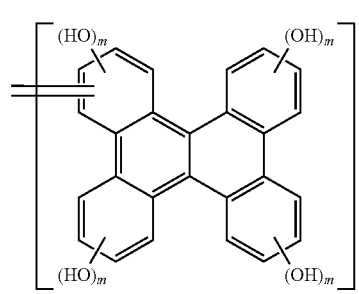
(3-4)
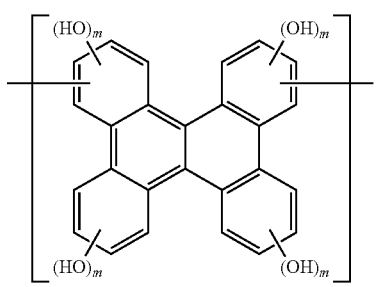
(3-9)
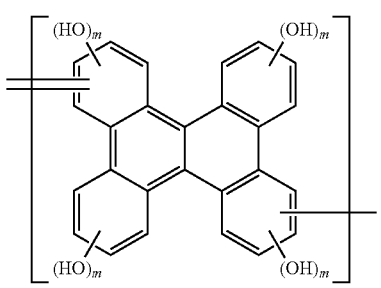
(3-5)
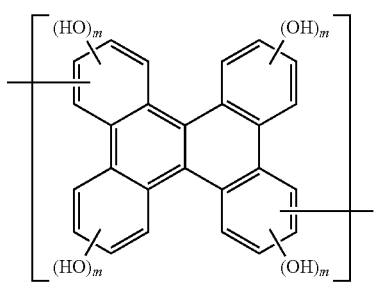
(3-10)
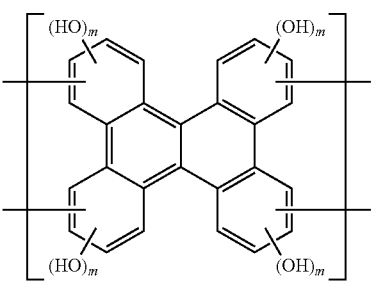
(3-6)
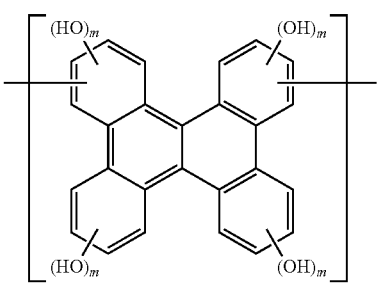
(3-11)
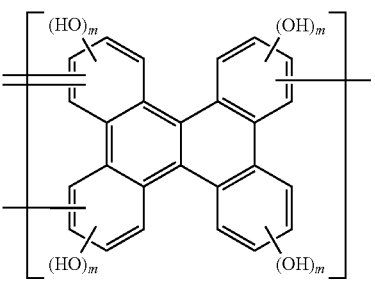

-continued

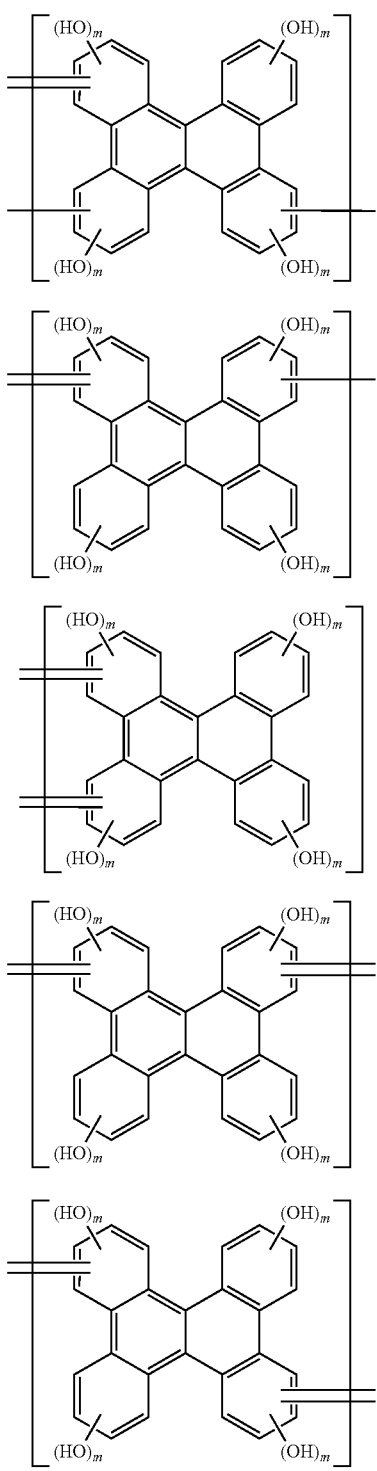

(3-12)

(3-13)

(3-14)

(3-15)

(3-16)

In the formulae (3-1) to (3-16), each m is independently an integer of 0 to 4, in which at least one m is an integer of 1 to 4.

Specific examples of the resin having any structure represented by the formulae (3-1) to (3-16) include a novolac resin obtained by a condensation reaction of the compound represented by the formula (2) with an aldehyde as the compound having crosslinking reactivity.

Herein, examples of the aldehyde for use in forming the novolac resin of the compound represented by the formula (2) include formaldehyde, trioxane, paraformaldehyde, benzaldehyde, acetaldehyde, propylaldehyde, phenylacetaldehyde, phenylpropylaldehyde, hydroxybenzaldehyde, chlorobenzaldehyde, nitrobenzaldehyde, methylbenzaldehyde, ethylbenzaldehyde, butylbenzaldehyde, biphenylaldehyde, naphthaldehyde, anthracenecarbaldehyde, phenanthrenecarbaldehyde, pyrenecarbaldehyde, and furfural, but are not limited thereto. Among them, formaldehyde is preferable. Herein, these aldehydes can be used alone, or two or more thereof can be used in combination. In addition, the amount of the aldehydes to be used is not particularly limited, but the amount is preferably 0.2 to 5 mol and more preferably 0.5 to 2 mol based on 1 mol of the compound represented by the formula (2).

A catalyst can also be used in the condensation reaction of the compound represented by the formula (2) with an aldehyde. The acid catalyst that can be here used is appropriately selected from known ones, and is not particularly limited. Such an acid catalyst is an inorganic acid or an organic acid, as widely known, and examples thereof include inorganic acids such as hydrochloric acid, sulfuric acid, phosphoric acid, hydrobromic acid, or hydrofluoric acid, organic acids such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, or naphthalenedisulfonic acid, Lewis acids such as zinc chloride, aluminum chloride, iron chloride, or boron trifluoride, or solid acids such as tungstosilicic acid, tungstophosphoric acid, silicomolybdic acid, or phosphomolybdic acid, but are not particularly limited thereto. Among them, organic acids and solid acids are preferable in terms of production, and hydrochloric acid or sulfuric acid is preferably used in terms of production such as availability or handleability.

Herein, these acid catalysts can be used alone, or two or more thereof can be used in combination. In addition, the amount of the acid catalyst to be used can be appropriately set depending on the types of raw materials to be used and the catalyst to be used, reaction conditions, and the like, and is not particularly limited, but the amount is preferably 0.01 to 100 parts by mass based on 100 parts by mass of reaction raw materials. Herein, in the case of copolymerization with a compound having a non-conjugated double bond, such as indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, 5-vinylnorborna-2-ene, α-pinene, β-pinene, and limonene, aldehydes may not necessarily be used.

A reaction solvent can also be used in the condensation reaction of the compound represented by the formula (2) with an aldehyde. The reaction solvent in the polycondensation, which can be used, is appropriately selected from known ones, and is not particularly limited, but examples thereof include water, methanol, ethanol, propanol, butanol, tetrahydrofuran, dioxane, or a mixed solvent thereof. Herein, these reaction solvents can be used alone, or two or more thereof can be used in combination. In addition, the amount of the reaction solvent to be used can be appropriately set depending on the types of raw materials to be used and the catalyst to be used, reaction conditions, and the like, and is not particularly limited, but the amount preferably ranges from 0 to 2000 parts by mass based on 100 parts by mass of reaction raw materials.

The reaction temperature can be appropriately selected depending on the reactivity of reaction raw materials, and is not particularly limited, but the reaction temperature usually ranges from 10 to 200° C. Herein, the reaction method that can be used is appropriately selected from known methods, and is not particularly limited, but includes a method in which the compound represented by the formula (2), the aldehydes, and the catalyst are charged at once, and a method in which the compound represented by the formula (2) and the aldehydes are dropped in the presence of the catalyst.

After completion of the polycondensation reaction, the resulting compound can be isolated according to an ordinary method, and the isolation method is not particularly limited. For example, in order to remove the unreacted raw materials and the catalyst present in the system, a common method in which the temperature in a reaction tank is raised to 130 to 230° C. to remove a volatile content at about 1 to 50 mmHg can be adopted to thereby provide an objective novolac resin.

Herein, the resin having any structure represented by the formulae (3-1) to (3-16) may be a homopolymer of the compound represented by the formula (2), or may be a copolymer thereof with other phenols. Examples of the copolymerizable phenols include phenol, cresol, dimethylphenol, trimethylphenol, butylphenol, phenylphenol, diphenylphenol, naphthylphenol, resorcinol, methylresorcinol, catechol, butylcatechol, methoxyphenol, methoxyphenol, propylphenol, pyrogallol, and thymol, but are not limited thereto.

In addition, the resin having any structure represented by the formulae (3-1) to (3-16) may be one obtained by copolymerization with a polymerizable monomer other than the above-described other phenols. Examples of such a copolymerizable monomer include naphthol, methylnaphthol, methoxynaphthol, dihydroxynaphthalene, indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, vinylnorbornaene, pinene, and limonene, but are not limited thereto. Herein, the resin having any structure represented by the formulae (3-1) to (3-16) may be a bi or higher functional (for example, bi to tetra) copolymer of the compound represented by the formula (2) with phenols, may be a bi or higher functional (for example, bi to tetra) copolymer of the compound represented by the formula (2) with the above-described copolymerizable monomer, or may be a ter or higher (for example, ter to tetra) copolymer of the compound represented by the formula (2), the above-described phenols, and the above-described copolymerizable monomer.

The molecular weight of the resin having any structure represented by the formulae (3-1) to (3-16) is not particularly limited, and the weight average molecular weight (Mw) in terms of polystyrene is preferably 500 to 300,000, and more preferably 750 to 200,000. In addition, the resin having any structure represented by the formulae (3-1) to (3-16) preferably has a dispersity (weight average molecular weight Mw/number average molecular weight Mn) in a range from 1.1 to 7 from the viewpoints of improving a crosslinking efficiency and suppressing a volatile component during baking. Herein, the Mw, the Mn and the dispersity (Mw/Mn) can be determined by a method in Examples described later.

The material for forming a film for lithography of the present embodiment preferably has a high solubility in a solvent from the viewpoint of making application of a wet process easier. More specifically, when 1-methoxy-2-propanol (PGME), and/or propylene glycol monomethyl ether acetate (PGMEA), and/or cyclopentanone (CPN), and/or cyclohexanone (CHN) are/is used for the solvent, the material for forming a film for lithography of the present embodiment (compound and/or resin) preferably has a solubility of 10% by mass or more in the solvent. Herein, the solubility in PGME and/or PGMEA, and/or CPN, and/or CHN is defined as "Mass of resin/(Mass of resin+Mass of solvent)× 100 (% by mass)". For example, in the case where 10 g of the material for forming a film for lithography is evaluated to be dissolved in 90 g of PGMEA, the solubility of the material for forming a film for lithography in PGMEA is "10% by mass or more", and in the case where the material is evaluated not to be dissolved, the solubility is "less than 10% by mass".

[Composition for Forming Film for Lithography]

A composition for forming a film for lithography of the present embodiment contains the material for forming a film for lithography of the present embodiment and an organic solvent.

The organic solvent is not particularly limited as long as it dissolves at least the material for forming a film for lithography of the present embodiment (compound and/or resin), and a known solvent can be appropriately used. Specific examples of the organic solvent include ketone-based solvents such as acetone, methyl ethyl ketone, methyl isobutyl ketone and cyclohexanone; cellosolve-based solvents such as propylene glycol monomethyl ether and propylene glycol monomethyl ether acetate; ester-based solvents such as ethyl lactate, methyl acetate, ethyl acetate, butyl acetate, isoamyl acetate, ethyl lactate, methyl methoxypropionate and methyl hydroxyisobutyrate; alcohol-based solvents such as methanol, ethanol, isopropanol and 1-ethoxy-2-propanol; and aromatic hydrocarbons such as toluene, xylene and anisole, but are not limited thereto. These organic solvents can be used singly or in combinations of two or more thereof.

Among the organic solvents, preferable are cyclohexanone, propylene glycol monomethyl ether, propylene glycol monomethyl ether acetate, ethyl lactate, methyl hydroxyisobutyrate, and anisole, in terms of safety.

The content of the organic solvent is not particularly limited, but it is preferably 100 to 10,000 parts by mass, more preferably 200 to 5,000 parts by mass based on 100 parts by mass of the material for forming a film for lithography of the present embodiment (compound and/or resin), in terms of solubility and film formation.

The composition for forming a film for lithography of the present embodiment may contain, if necessary, other component such as a crosslinking agent and an acid generating agent, other than the material for forming a film for lithography of the present embodiment and the organic solvent. Hereinafter, these optional components will be described.

The composition for forming a film for lithography of the present embodiment may contain, if necessary, a crosslinking agent from the viewpoint of suppression of intermixing, and the like. Specific examples of the crosslinking agent usable in the present embodiment include a melamine compound, a guanamine compound, a glycoluril compound, a urea compound, an epoxy compound, a thioepoxy compound, an isocyanate compound, an azide compound, and a compound including a double bond such as an alkenyl ether group, these compounds being substituted with at least one group selected from a methylol group, an alkoxymethyl group and an acyloxymethyl group, as a substituent (crosslinkable group), but are not limited thereto. Herein, these crosslinking agents can be used singly or in combinations of two or more thereof. Such a crosslinking agent can also be used as an additive. Herein, the crosslinkable group may also be introduced as a pendant group into a polymer side chain of the compound represented by the formula (1) and/or the resin having any structure represented by the formulae (3-1) to (3-16). A compound including a hydroxy group can also be used as the crosslinking agent.

Specific examples of the melamine compound include, but are not limited to the following, hexamethylolmelamine, hexamethoxymethylmelamine, a compound in which 1 to 6 methylol groups in hexamethylolmelamine are methoxymethylated, or mixtures thereof, and hexamethoxyethylmelamine, hexaacyloxymethylmelamine, a compound in which 1 to 6 methylol groups in hexamethylolmelamine are acyloxymethylated, or mixtures thereof. Specific examples of the epoxy compound include, but are not limited to the following, tris(2,3-epoxypropyl)isocyanurate, trimethylolmethane triglycidyl ether, trimethylolpropane triglycidyl ether, and triethylolethane triglycidyl ether.

Specific examples of the guanamine compound include, but are not limited to the following, tetramethylolguanamine, tetramethoxymethylguanamine, a compound in which 1 to 4 methylol groups in tetramethylolguanamine are methoxymethylated, or mixtures thereof, and tetramethoxyethylguanamine, tetraacyloxyguanamine, a compound in which 1 to 4 methylol groups in tetramethylolguanamine are acyloxymethylated, or mixtures thereof. Specific examples of the glycoluril compound include, but are not limited to the following, tetramethylolglycoluril, tetramethoxyglycoluril, tetramethoxymethylglycoluril, a compound in which 1 to 4 methylol groups in tetramethylolglycoluril are methoxymethylated, or mixtures thereof, and a compound in which 1 to 4 methylol groups in tetramethylolglycoluril are acyloxymethylated, or mixtures thereof. Specific examples of the urea compound include, but are not limited to the following, tetramethylolurea, tetramethoxymethylurea, a compound in which 1 to 4 methylol groups in tetramethylolurea are methoxymethylated, or mixtures thereof, and tetramethoxyethylurea.

Specific examples of the compound including an alkenyl ether group include, but are not limited to the following, ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylolpropane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylolpropane trivinyl ether.

In the composition for forming a film for lithography according to the present embodiment, the content of the crosslinking agent is not particularly limited, but the content is preferably 5 to 50 parts by mass and more preferably 10 to 40 parts by mass based on 100 parts by mass of the material for forming a film for lithography of the present embodiment (compound and/or resin). The content is set within the above preferable range to result in tendencies to suppress the occurrence of the mixing phenomenon with the resist layer, and to result in tendencies to enhance an antireflective effect and improve film formability after crosslinking.

The composition for forming a film for lithography of the present embodiment may also contain, if necessary, an acid generating agent from the viewpoint of further promoting a crosslinking reaction by heat. As the acid generating agent, one for generating an acid by pyrolysis and one for generating an acid by light irradiation are known, and any of them can be used.

The acid generating agent includes:
1) an onium salt of the following general formula (P1a-1), (P1a-2), (P1a-3) or (P1b),
2) a diazomethane derivative of the following general formula (P2),
3) a glyoxime derivative of the following general formula (P3),
4) a bissulfone derivative of the following general formula (P4),
5) a sulfonic acid ester of an N-hydroxyimide compound of the following general formula (P5),
6) a β-ketosulfonic acid derivative,
7) a disulfone derivative,
8) a nitrobenzylsulfonate derivative, and
9) a sulfonic acid ester derivative, but is not limited thereto. Herein, these acid generating agents can be used alone, or two or more thereof can be used in combination.

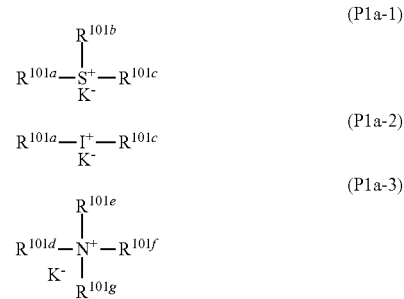

(In the above formulae, each of $R^{101a}$, $R^{101b}$ and $R^{101c}$ independently represents a straight, branched or cyclic alkyl group, alkenyl group, oxoalkyl group or oxoalkenyl group having 1 to 12 carbon atoms; an aryl group having 6 to 20 carbon atoms; or an aralkyl group or aryloxoalkyl group having 7 to 12 carbon atoms, and a part or all of hydrogen atoms of these groups may be substituted with an alkoxy group or the like. In addition, $R^{101b}$ and $R^{101c}$ may form a ring, and if forming a ring, each of $R^{101b}$ and $R^{101c}$ independently represents an alkylene group having 1 to 6 carbon atoms. $K^-$ represents a non-nucleophilic counter ion. $R^{101d}$, $R^{101e}$, $R^{101f}$ and $R^{101g}$ are represented by each independently adding a hydrogen atom to $R^{101a}$, $R^{101b}$ and $R^{101c}$. $R^{101d}$ and $R^{101e}$, and $R^{101d}$, $R^{101e}$ and $R^{101f}$ may form a ring, and if forming a ring, $R^{101d}$ and $R^{101e}$, and $R^{101d}$, $R^{101e}$ and $R^{101f}$ represent an alkylene group having 3 to 10 carbon atoms, or a heteroaromatic ring having therein the nitrogen atom(s) in the formula.)

$R^{101a}$, $R^{101b}$, $R^{101c}$, $R^{101d}$, $R^{101e}$, $R^{101f}$ and $R^{101g}$ described above may be the same or different from one another. Specifically, examples of the alkyl group include, but are not limited to the following, a methyl group, an ethyl group, a propyl group, an isopropyl group, a n-butyl group, a sec-butyl group, a tert-butyl group, a pentyl group, a hexyl group, a heptyl group, an octyl group, a cyclopentyl group, a cyclohexyl group, a cycloheptyl group, a cyclopropylmethyl group, a 4-methyl cyclohexyl group, a cyclohexylmethyl group, a norbornyl group, and an adamantyl group. Examples of the alkenyl group include, but are not limited to the following, a vinyl group, an allyl group, a propenyl group, a butenyl group, a hexenyl group, and a cyclohexenyl group. Examples of the oxoalkyl group can include, but are not limited to the following, a 2-oxocyclopentyl group, a 2-oxocyclohexyl group, a 2-oxopropyl group, a 2-cyclopentyl-2-oxoethyl group, a 2-cyclohexyl-2-oxoethyl group, and a 2-(4-methylcyclohexyl)-2-oxoethyl group. Examples of the oxoalkenyl group include, but are not limited to the following, a 2-oxo-4-cyclohexenyl group and a 2-oxo-4-propenyl group. Examples of the aryl group include, but are not limited to the following, a phenyl group, a naphthyl group, alkoxyphenyl groups such as a p-methoxyphenyl group, a m-methoxyphenyl group, an o-methoxyphenyl group, an ethoxyphenyl group, a p-tert-butoxyphenyl group, and a m-tert-butoxyphenyl group; alkylphenyl groups such as a 2-methylphenyl group, a 3-methylphenyl group, a 4-methylphenyl group, an ethylphenyl group, a 4-tert-butyl-phenyl group, a 4-butylphenyl group, and a dimethylphenyl group; alkylnaphthyl groups such as a methylnaphthyl group and an ethylnaphthyl group; alkoxynaphthyl groups such as a methoxynaphthyl group and an ethoxynaphthyl group; dialkylnaphthyl groups such as a dimethylnaphthyl group and a diethylnaphthyl group; and dialkoxynaphthyl groups such as a dimethoxynaphthyl group and a diethoxynaphthyl group. Examples of the aralkyl group include, but are not limited to the following, a benzyl group, a phenylethyl group, and a phenethyl group. Examples of the aryloxoalkyl group include, but are not limited to the following, 2-aryl-2-oxoethyl groups such as a 2-phenyl-2-oxoethyl group, a 2-(1-naphthyl)-2-oxoethyl group, and a 2-(2-naphthyl)-2-oxoethyl group. Examples of the non-nucleophilic counter ion, $K^-$, include, but are not limited to the following, halide ions such as a chloride ion and a bromide ion; fluoroalkyl sulfonates such as triflate, 1,1,1-trifluoroethane sulfonate, and nonafluorobutane sulfonate; aryl sulfonates such as tosylate, benzene sulfonate, 4-fluorobenzene sulfonate, and 1,2,3,4,5-pentafluorobenzene sulfonate; and alkyl sulfonates such as mesylate and butane sulfonate.

In the case where $R^{101d}$, $R^{101e}$, $R^{101f}$ and $R^{101g}$ are each a heteroaromatic ring having the nitrogen atom(s) in the formula, examples of the heteroaromatic ring include imidazole derivatives (for example, imidazole, 4-methylimidazole, and 4-methyl-2-phenylimidazole), pyrazole derivatives, furazan derivatives, pyrroline derivatives (for example, pyrroline and 2-methyl-1-pyrroline), pyrrolidine derivatives (for example, pyrrolidine, N-methylpyrrolidine, pyrrolidinone, and N-methylpyrrolidone), imidazoline derivatives, imidazolidine derivatives, pyridine derivatives (for example, pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (for example, quinoline and 3-quinolinecarbonitrile), isoquinoline derivatives, cinnoline derivatives, quinazoline derivatives, quinoxaline derivatives, phthalazine derivatives, purine derivatives, pteridin derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivative, and uridine derivatives.

The onium salts of the formula (P1a-1) and the formula (P1a-2) have functions as a photo acid generating agent and a thermal acid generating agent. The onium salt of the formula (P1a-3) has a function as a thermal acid generating agent.

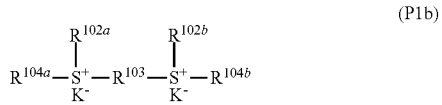

(P1b)

(In the formula (P1b), each of $R^{102a}$ and $R^{102b}$ independently represents a straight, branched or cyclic alkyl group having 1 to 8 carbon atoms. $R^{103}$ represents a straight, branched or cyclic alkylene group having 1 to 10 carbon atoms. Each of $R^{104a}$ and $R^{104b}$ independently represents a 2-oxoalkyl group having 3 to 7 carbon atoms. $K^-$ represents a non-nucleophilic counter ion.)

Specific examples of $R^{102a}$ and $R^{102b}$ include, but are not limited to the following, a methyl group, an ethyl group, a propyl group, an isopropyl group, a n-butyl group, a sec-butyl group, a tert-butyl group, a pentyl group, a hexyl group, a heptyl group, an octyl group, a cyclopentyl group, a cyclohexyl group, a cyclopropylmethyl group, a 4-methyl cyclohexyl group, and a cyclohexylmethyl group. Specific examples of $R^{103}$ include, but are not limited to the following, a methylene group, an ethylene group, a propylene group, a butylene group, a pentylene group, a hexylene group, a heptylene group, an octylene group, a nonylene group, a 1,4-cyclohexylene group, a 1,2-cyclohexylene group, a 1,3-cyclopentylene group, a 1,4-cyclooctylene group, and a 1,4-cyclohexanedimethylene group. Specific examples of $R^{104a}$ and $R^{104b}$ include, but are not limited to the following, a 2-oxopropyl group, a 2-oxocyclopentyl group, a 2-oxocyclohexyl group, and a 2-oxocycloheptyl group. $K^-$ includes the same as those described in the formula (P1a-1), (P1a-2) and (P1a-3).

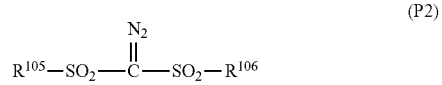

(P2)

In the formula (P2), each of $R^{105}$ and $R^{106}$ independently represents a straight, branched or cyclic alkyl group or halogenated alkyl group having 1 to 12 carbon atoms, an aryl group or halogenated aryl group having 6 to 20 carbon atoms, or an aralkyl group having 7 to 12 carbon atoms.

Examples of the alkyl group in each of $R^{105}$ and $R^{106}$ include, but are not limited to the following, a methyl group, an ethyl group, a propyl group, an isopropyl group, a n-butyl group, a sec-butyl group, a tert-butyl group, a pentyl group, a hexyl group, a heptyl group, an octyl group, an amyl group, a cyclopentyl group, a cyclohexyl group, a cycloheptyl group, a norbornyl group, and an adamantyl group. Examples of the halogenated alkyl group include, but are not limited to the following, a trifluoromethyl group, a 1,1,1-trifluoroethyl group, a 1,1,1-trichloroethyl group, and a nonafluorobutyl group. Examples of the aryl group include, but are not limited to the following, alkoxyphenyl groups such as a phenyl group, a p-methoxyphenyl group, a m-methoxyphenyl group, an o-methoxyphenyl group, an ethoxyphenyl group, a p-tert-butoxyphenyl group, and a m-tert-butoxyphenyl group; and alkylphenyl groups such as a 2-methylphenyl group, a 3-methylphenyl group, a 4-methylphenyl group, an ethylphenyl group, a 4-tert-butylphenyl group, a 4-butylphenyl group, and a dimethylphenyl group. Examples of the halogenated aryl group include, but are not limited to the following, a fluorophenyl group, a chlorophenyl group, and a 1,2,3,4,5-pentafluorophenyl group. Examples of the aralkyl group include, but are not limited to the following, a benzyl group and a phenethyl group.

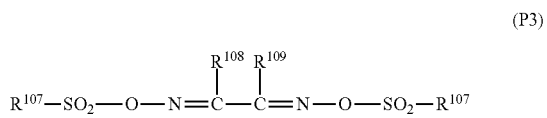

(P3)

In the formula (P3), each of $R^{107}$, $R^{108}$ and $R^{109}$ independently represents a straight, branched or cyclic alkyl group or halogenated alkyl group having 1 to 12 carbon atoms; an aryl group or halogenated aryl group having 6 to 20 carbon atoms; or an aralkyl group having 7 to 12 carbon atoms. $R^{108}$ and $R^{109}$ may be bonded with each other to form a cyclic structure, and if forming a cyclic structure, each of $R^{108}$ and $R^{109}$ represents a straight or branched alkylene group having 1 to 6 carbon atoms.

The alkyl group, halogenated alkyl group, aryl group, halogenated aryl group, and aralkyl group in each of $R^{107}$, $R^{108}$ and $R^{109}$ include the same as those described in $R^{105}$ and $R^{106}$. Herein, examples of the alkylene group in each of $R^{108}$ and $R^{109}$ include, but are not limited to the following, a methylene group, an ethylene group, a propylene group, a butylene group, and a hexylene group.

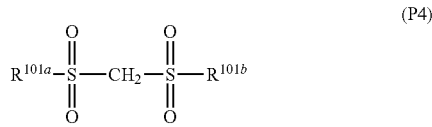

(P4)

In the formula (P4), $R^{101a}$ and $R^{101b}$ are the same as those described above.

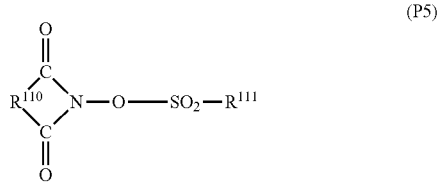

(P5)

In the formula (P5), $R^{110}$ represents an arylene group having 6 to 10 carbon atoms, an alkylene group having 1 to 6 carbon atoms, or an alkenylene group having 2 to 6 carbon atoms, and a part or all of hydrogen atoms of these groups may be further substituted with a straight or branched alkyl group or alkoxy group having 1 to 4 carbon atoms, a nitro group, an acetyl group, or a phenyl group. $R^{111}$ represents a straight, branched or substituted alkyl group, alkenyl group or alkoxyalkyl group having 1 to 8 carbon atoms, a phenyl group, or a naphthyl group, and a part or all of hydrogen atoms of these groups may be further substituted with an alkyl group or alkoxy group having 1 to 4 carbon atoms; a phenyl group that may be substituted with an alkyl group or alkoxy group having 1 to 4 carbon atoms, a nitro group, or an acetyl group; a heteroaromatic group having 3 to 5 carbon atoms; or a chlorine atom or a fluorine atom.

Herein, examples of the arylene group in $R^{110}$ include, but are not limited to the following, a 1,2-phenylene group and a 1,8-naphthylene group. Examples of the alkylene group include, but are not limited to the following, a methylene group, an ethylene group, a trimethylene group, a tetramethylene group, a phenylethylene group, and a norbornane-2,3-diyl group. Examples of the alkenylene group include, but are not limited to the following, a 1,2-vinylene group, a 1-phenyl-1,2-vinylene group, and a 5-norbornene-2,3-diyl group. The alkyl group in Rill includes the same as those in $R^{101a}$ to $R^{101c}$. Examples of the alkenyl group include, but are not limited to the following, a vinyl group, a 1-propenyl group, an allyl group, a 1-butenyl group, a 3-butenyl group, an isoprenyl group, a 1-pentenyl group, a 3-pentenyl group, a 4-pentenyl group, a dimethylallyl group, a 1-hexenyl group, a 3-hexenyl group, a 5-hexenyl group, a 1-heptenyl group, a 3-heptenyl group, a 6-heptenyl group, and a 7-octenyl group. Examples of the alkoxyalkyl group include, but are not limited to the following, a methoxymethyl group, an ethoxymethyl group, a propoxymethyl group, a butoxymethyl group, a pentyloxymethyl group, a hexyloxymethyl group, a heptyloxymethyl group, a methoxyethyl group, an ethoxyethyl group, a propoxyethyl group, a butoxyethyl group, a pentyloxyethyl group, a hexyloxyethyl group, a methoxypropyl group, an ethoxypropyl group, a propoxypropyl group, a butoxypropyl group, a methoxybutyl group, an ethoxybutyl group, a propoxybutyl group, a methoxypentyl group, an ethoxypentyl group, a methoxyhexyl group, and a methoxyheptyl group.

Herein, Examples of the alkyl group having 1 to 4 carbon atoms, which may be further substituted, include, but are not limited to the following, a methyl group, an ethyl group, a propyl group, an isopropyl group, a n-butyl group, a an isobutyl group, and a tert-butyl group. Examples of the alkoxy group having 1 to 4 carbon atoms include, but are not limited to the following, a methoxy group, an ethoxy group, a propoxy group, an isopropoxy group, a n-butoxy group, an isobutoxy group, and tert-butoxy group. Examples of the phenyl group that may be substituted with an alkyl group or alkoxy group having 1 to 4 carbon atoms, a nitro group, or an acetyl group include, but are not limited to the following, a phenyl group, a tolyl group, a p-tert-butoxyphenyl group, a p-acetylphenyl group, and a p-nitrophenyl group. Examples of the heteroaromatic group having 3 to 5 carbon atoms include, but are not limited to the following, a pyridyl group and a furyl group.

Specific examples of the acid generating agent include, but are not limited to the following, onium salts such as tetramethylammonium trifluoromethanesulfonate, tetramethylammonium nonafluorobutanesulfonate, triethylammonium nonafluorobutanesulfonate, pyridinium nonafluorobutanesulfonate, triethylammonium camphorsulfonate, pyridinium camphorsulfonate, tetra n-butylammonium nonafluorobutanesulfonate, tetraphenylammonium nonafluorobutanesulfonate, tetramethylammonium p-toluenesulfonate, diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl) diphenylsulfonium trifluoromethanesulfonate, bis(p-tert-butoxyphenyl)phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris (p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, ethylene bis [methyl(2-oxocyclopentyl)sulfonium trifluoromethanesulfonate], and 1,2'-naphthylcarbonylmethyltetrahydrothiophenium triflate; diazomethane derivatives such as bis(benzenesulfonyl)diazomethane, bis(p-toluenesulfonyl)diazomethane, bis(xylenesulfonyl)diazomethane, bis(cyclohexylsulfonyl)diazomethane, bis(cyclopentylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, bis(tert-butylsulfonyl)diazomethane, bis(n-amylsulfonyl)diazomethane, bis(isoamylsulfonyl)diazomethane, bis(sec-amylsulfonyl)diazomethane, bis(tert-amylsulfonyl)diazomethane, 1-cyclohexylsulfonyl-1-(tert-butylsulfonyl)diazomethane, 1-cyclohexylsulfonyl-1-(tert-amylsulfonyl)diazomethane, and 1-tert-amylsulfonyl-1-(tert-butylsulfonyl)diazomethane; glyoxime derivatives such as bis-(p-toluenesulfonyl)-α-dimethylglyoxime, bis-(p-toluesulfonyl)-α-diphenylglyoxime, bis-(p-toluenesulfonyl)-α-dicyclohexylglyoxime, bis-(p-toluenesulfonyl)-2,3-pentanedioneglyoxime, bis-(p-toluenesulfonyl)-2-methyl-3,4-pentanedioneglyoxime, bis-(n-butanesulfonyl)-α-dimethylglyoxime, bis-(n-butanesulfonyl)-α-diphenylglyoxime, bis-(n-butanesulfonyl)-α-dicyclohexylglyoxime, bis-(n-butanesulfonyl)-2,3-pentanedioneglyoxime, bis-(n-butanesulfonyl)-2-methyl-3,4-pentanedioneglyoxime, bis-(methanesulfonyl)-α-dimethylglyoxime, bis-(trifluoromethanesulfonyl)-α-dimethylglyoxime, bis-(1,1,1-trifluoroethanesulfonyl)-α-dimethylglyoxime, bis-(tert-butanesulfonyl)-α-dimethylglyoxime, bis-(perfluorooctanesulfonyl)-α-dimethylglyoxime, bis-(cyclohexanesulfonyl)-α-dimethylglyoxime, bis-(benzenesulfonyl)-α-dimethylglyoxime, bis-(p-fluorobenzenesulfonyl)-α-dimethylglyoxime, bis-(p-tert-butylbenzenesulfonyl)-α-dimethylglyoxime, bis-(xylenesulfonyl)-α-dimethylglyoxime, and bis-(camphorsulfonyl)-α-dimethylglyoxime; bissulfone derivatives, such as bisnaphthylsulfonylmethane, bistrifluoromethylsulfonylmethane, bismethylsulfonylmethane, bisethylsulfonylmethane, bispropylsulfonylmethane, bisisopropylsulfonylmethane, bis-p-toluenesulfonylmethane, and bisbenzenesulfonylmethane; β-ketosulfone derivatives such as 2-cyclohexylcarbonyl-2-(p-toluenesulfonyl)propane and 2-isopropylcarbonyl-2-(p-toluenesulfonyl)propane; disulfone derivatives such as a diphenyldisulfone derivative and a dicyclohexyldisulfone derivative, nitrobenzylsulfonate derivatives such as 2,6-dinitrobenzyl p-toluenesulfonate and 2,4-dinitrobenzyl p-toluenesulfonate; sulfonic acid ester derivatives such as 1,2,3-tris(methanesulfonyloxy)benzene, 1,2,3-tris(trifluoromethanesulfonyloxy)benzene, and 1,2,3-tris(p-toluenesulfonyloxy)benzene; and sulfonic acid ester derivatives of a N-hydroxyimide compound, such as N-hydroxysuccinimide methanesulfonic acid ester, N-hydroxysuccinimide trifluoromethanesulfonic acid ester, N-hydroxysuccinimide ethanesulfonic acid ester, N-hydroxysuccinimide 1-propanesulfonic acid ester, N-hydroxysuccinimide 2-propanesulfonic acid ester, N-hydroxysuccinimide 1-pentanesulfonic acid ester, N-hydroxysuccinimide 1-octanesulfonic acid ester, N-hydroxysuccinimide p-toluenesulfonic acid ester, N-hydroxysuccinimide p-methoxybenzenesulfonic acid ester, N-hydroxysuccinimide 2-chloroethanesulfonic acid ester, N-hydroxysuccinimide benzenesulfonic acid ester, N-hydroxysuccinimide-2,4,6-trimethylbenzenesulfonic acid ester, N-hydroxysuccinimide 1-naphthalenesulfonic acid ester, N-hydroxysuccinimide 2-naphthalenesulfonic acid ester, N-hydroxy-2-phenylsuccinimide methanesulfonic acid ester, N-hydroxymaleimide methanesulfonic acid ester, N-hydroxymaleimide ethanesulfonic acid ester, N-hydroxy-2-phenylmaleimide methanesulfonic acid ester, N-hydroxyglutarimide methanesulfonic acid ester, N-hydroxyglutarimide benzenesulfonic acid ester, N-hydroxyphthalimide methanesulfonic acid ester, N-hydroxyphthalimide benzenesulfonic acid ester, N-hydroxyphthalimide trifluoromethanesulfonic acid ester, N-hydroxyphthalimide p-toluenesulfonic acid ester, N-hydroxynaphthalimide methanesulfonic acid ester, N-hydroxynaphthalimide benzenesulfonic acid ester, N-hydroxy-5-norbornene-2,3-dicarboxyimide methanesulfonic acid ester, N-hydroxy-5-norbornene-2,3-dicarboxyimide trifluoromethanesulfonic acid ester, and N-hydroxy-5-norbornene-2,3-dicarboxyimide p-toluenesulfonic acid ester.

Among them, in particular, onium salts such as triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, tris(p-tert-butoxyphenyl)sulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, and 1,2'-naphthylcarbonylmethyltetrahydrothiophenium triflate; diazomethane derivatives such as bis(benzenesulfonyl)diazomethane, bis(p-toluenesulfonyl)diazomethane, bis(cyclohexylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, and bis(tert-butylsulfonyl)diazomethane; glyoxime derivatives such as bis-(p-toluenesulfonyl)-α-dimethylglyoxime and bis-(n-butanesulfonyl)-α-dimethylglyoxime, bissulfone derivatives such as bisnaphthylsulfonylmethane; and sulfonic acid ester derivatives of an N-hydroxyimide compound, such as N-hydroxysuccinimide methanesulfonic acid ester, N-hydroxysuccinimide trifluoromethanesulfonic acid ester, N-hydroxysuccinimide 1-propanesulfonic acid ester, N-hydroxysuccinimide 2-propanesulfonic acid ester, N-hydroxysuccinimide 1-pentanesulfonic acid ester, N-hydroxysuccinimide p-toluenesulfonic acid ester, N-hydroxynaphthalimide methanesulfonic acid ester, and N-hydroxynaphthalimide benzenesulfonic acid ester, and the like are preferably used.

In the composition for forming a film for lithography according to the present embodiment, the content of the acid generating agent is not particularly limited, but the content is preferably 0.1 to 50 parts by mass and more preferably 0.5 to 40 parts by mass based on 100 parts by mass of the material for forming a film for lithography of the present embodiment (compound and/or resin). The content is set within the above range to result in a tendency to increase the acid generation amount to promote a crosslinking reaction, and also to result in a tendency to suppress the occurrence of the mixing phenomenon with a resist layer.

Furthermore, the composition for forming a film for lithography of the present embodiment may contain a basic compound from the viewpoint of improving preservation stability.

The basic compound serves as a quencher to an acid for preventing a trace amount of the acid generated from the acid generating agent from promoting a crosslinking reaction. Examples of such a basic compound include primary, secondary, and tertiary aliphatic amines, mixed amines, aromatic amines, heterocyclic amines, a nitrogen-containing compound having a carboxy group, a nitrogen-containing compound having a sulfonyl group, a nitrogen-containing compound having a hydroxyl group, a nitrogen-containing compound having a hydroxyphenyl group, an alcoholic nitrogen-containing compound, an amide derivative, and an imide derivative, but are not limited thereto.

Specifically, specific examples of the primary aliphatic amines include, but are not limited to the following, ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Specific examples of the secondary aliphatic amines include, but are not limited to the following, dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Specific examples of the tertiary aliphatic amines include, but are not limited to the following, trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Specific examples of the mixed amines include, but are not limited to the following, dimethylethylamine, methylethylpropylamine, benzylamine, phenethylamine, and benzyldimethylamine. Specific examples of the aromatic amines and heterocyclic amines include, but are not limited to the following, aniline derivatives (for example, aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (for example, pyrrole, 2H-pyrrole, 1-methylpyrrole, 2,4-dimethylpyrrole, 2,5-dimethylpyrrole, and N-methylpyrrole), oxazole derivatives (for example, oxazole and isoxazole), thiazole derivatives (for example, thiazole and isothiazole), imidazole derivatives (for example, imidazole, 4-methylimidazole, and 4-methyl-2-phenylimidazole), pyrazole derivatives, furazan derivatives, pyrroline derivatives (for example, pyrroline and 2-methyl-1-pyrroline), pyrrolidine derivatives (for example, pyrrolidine, N-methylpyrrolidine, pyrrolidinone, and N-methylpyrrolidone), imidazoline derivatives, imidazolidine derivatives, pyridine derivatives (for example, pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (for example, quinoline, 3-quinolinecarbonitrile), isoquinoline derivatives, cinnoline derivatives, quinazoline derivatives, quinoxaline derivatives, phthalazine derivatives, purine derivatives, pteridin derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Furthermore, specific examples of the nitrogen-containing compound having a carboxy group include, but are not limited to the following, aminobenzoic acid, indolecarboxylic acid, and amino acid derivatives (for example, nicotinic acid, alanine, arginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Specific examples of the nitrogen-containing compound having a sulfonyl group include, but are not limited to the following, 3-pyridinesulfonic acid and pyridinium p-toluenesulfonate. Specific examples of the nitrogen-containing compound having a hydroxyl group, the nitrogen-containing compound having a hydroxyphenyl group, and the alcoholic nitrogen-containing compound include, but are not limited to the following, 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Specific examples of the amide derivative include, but are not limited to the following, formamide, N-methylformamide, N,N-dimethylformamide, acetamide, N-methylacetamide, N,N-dimethylacetamide, propionamide, and benzamide. Specific examples of the imide derivative include, but are not limited to the following, phthalimide, succinimide, and maleimide.

In the composition for forming a film for lithography according to the present embodiment, the content of the basic compound is not particularly limited, but the content is preferably 0.001 to 2 parts by mass and more preferably 0.01 to 1 part by mass based on 100 parts by mass of the material for forming a film for lithography of the present embodiment (compound and/or resin). The content is set within the above preferable range to result in a tendency to improve preservation stability without excessively interrupting a crosslinking reaction.

In addition, the composition for forming a film for lithography of the present embodiment may contain other resins and/or compounds for the purpose of imparting heat curability and controlling absorbance. Such other resins and/or compounds include naphthol resins, xylene resins, naphthol-modified resins, phenol-modified resins of naphthalene resins, polyhydroxystyrene, dicyclopentadiene resins, (meth)acrylate, dimethacrylate, trimethacrylate, tetramethacrylate, resins having a naphthalene ring such as vinylnaphthalene and polyacenaphthylene, resins having a biphenyl ring such as phenanthrenequinone and fluorene, resins having a heterocyclic ring having a hetero atom such as thiophene and indene, and resins not containing an aromatic ring; rosin-based resins, and resins or compounds including an alicyclic structure, such as cyclodextrin, adamantane(poly)ol, tricyclodecane(poly)ol and derivatives thereof, but are not limited thereto. Furthermore, the composition for forming a film for lithography of the present embodiment can also contain a known additive. Examples of the known additive includes, but not limited to the following, an ultraviolet absorber, a surfactant, a colorant and a non-ionic surfactant.

[Forming Method of Underlayer Film for Lithography and Pattern]

A film for lithography of the present embodiment is formed by using the composition for forming a film for lithography of the present embodiment.

In addition, a resist pattern forming method of the present embodiment comprises step (A-1) of forming a film on a substrate by using the composition for forming a film for lithography of the present embodiment, step (A-2) of forming at least one photoresist layer on the film, and step (A-3) of, after the second forming step, irradiating a predetermined region of the photoresist layer with radiation, followed by developing.

Furthermore, a circuit pattern forming method of the present embodiment comprises step (B-1) of forming a film on a substrate by using the composition for forming a film for lithography of the present embodiment, step (B-2) of forming an intermediate layer film on the film by using a silicon atom-containing resist intermediate layer film material, step (B-3) of forming at least one photoresist layer on the intermediate layer film, step (B-4) of, after step (B-3), irradiating a predetermined region of the photoresist layer with radiation, followed by developing to form a resist pattern, and step (B-5) of, after step (B-4), etching the intermediate layer film with the resist pattern as a mask, etching the film with the obtained intermediate layer film pattern as an etching mask and etching the substrate with the obtained film pattern as an etching mask, to form a pattern on the substrate.

The film for lithography of the present embodiment is not particularly limited in terms of the forming method thereof as long as it is formed from the composition for forming a film for lithography of the present embodiment, and a known method can be applied. For example, the film for lithography can be formed by applying the composition for forming a film for lithography of the present embodiment on the substrate by a known coating method or printing method such as spin coating or screen printing, and removing an organic solvent by volatilization or the like.

The film for lithography is preferably baked upon forming in order to suppress the occurrence of the mixing phenomenon with an upperlayer resist and also promote a crosslinking reaction. In this case, the baking temperature is not particularly limited, but it is preferably within the range of 80 to 450° C., and more preferably 200 to 400° C. In addition, the baking time is not also particularly limited, but is preferably within the range of 10 to 300 seconds. Herein, the thickness of the underlayer film can be appropriately selected depending on the required properties, and is not particularly limited, but the thickness is usually preferably about 30 to 20,000 nm and more preferably 50 to 15,000 nm.

After the film for lithography is prepared on the substrate, preferably, in the case of a two-layer process, a silicon-containing resist layer or a usual single-layer resist including a hydrocarbon is prepared on the film for lithography, and in the case of a three-layer process, a silicon-containing intermediate layer is prepared on the film for lithography and a single-layer resist layer not containing silicon is further prepared on the silicon-containing intermediate layer. In these cases, a photoresist material for forming the resist layer, which can be used, is a known one.

As the silicon-containing resist material for a two-layer process, a positive-type photoresist material is preferably used, which contains a silicon atom-containing polymer such as a polysilsesquioxane derivative or a vinylsilane derivative used as a base polymer in the viewpoint of oxygen gas-etching resistance, and an organic solvent, an acid generating agent and if necessary a basic compound. Herein, as the silicon atom-containing polymer, a known polymer used in such a resist material can be used.

As the silicon-containing intermediate layer for a three-layer process, a polysilsesquioxane-based intermediate layer is preferably used. The intermediate layer is allowed to have an effect as an antireflective film, and thus tends to make it possible to effectively suppress reflection. For example, if a material including many aromatic groups and having a high substrate-etching resistance is used for the underlayer film in a 193 nm exposure process, a k-value tends to be increased to increase substrate reflection rate, but the reflection can be suppressed by the intermediate layer to thereby make the substrate reflection rate 0.5% or less. For the intermediate layer having such an antireflection effect, but not limited to the following, polysilsesquioxane into which a phenyl group or a light-absorbing group having a silicon-silicon bond for 193 nm exposure is introduced and which is to be crosslinked with an acid or heat is preferably used.

An intermediate layer formed by the Chemical Vapour Deposition (CVD) method can also be used. As the intermediate layer having a high effect as an antireflective film, prepared by the CVD method, but not limited to the following, for example, a SiON film is known. In general, the intermediate layer is formed by a wet process such as a spin coating method or screen printing rather than the CVD method in terms of simplicity and cost effectiveness. Herein, the upperlayer resist in a three-layer process may be of positive-type or negative-type, and the same one as a commonly used single-layer resist can be used therefor.

Furthermore, the film for lithography of the present embodiment can also be used as a usual antireflective film for use in a single-layer resist or a usual underlying material for suppressing pattern collapse. The film for lithography of the present embodiment can also be expected to serve as a hard mask for underlying processing because of being excellent in etching resistance for underlying processing.

In the case where a resist layer is formed by the photoresist material, a wet process such as a spin coating method or screen printing is preferably used as in the case of forming the film for lithography. The resist material is coated by a spin coating method or the like and then usually pre-baked, and such pre-baking is preferably performed in the range of 80 to 180° C. for 10 to 300 seconds. Thereafter, in accordance with an ordinary method, the resultant can be subjected to exposure, post-exposure bake (PEB), and development to obtain a resist pattern. Herein, the thickness of the resist film is not particularly limited, but generally, it is preferably 30 to 500 nm and more preferably 50 to 400 nm.

Light for use in exposure may be appropriately selected depending on the photoresist material to be used. In general, examples thereof include high energy radiation having a wavelength of 300 nm or less, specifically, excimer lasers of 248 nm, 193 nm, and 157 nm, a soft X-ray of 3 to 20 nm, electron beam, and an X-ray.

The resist pattern formed by the above method is a pattern whose collapse is suppressed by the film for lithography of the present embodiment. Therefore, the film for lithography of the present embodiment can be used to thereby obtain a finer pattern, and an exposure amount necessary for obtaining such a resist pattern can be reduced.

Then, the obtained resist pattern is used as a mask to perform etching. As the etching of the underlayer film in a two-layer process, gas etching is preferably used. As the gas etching, etching using oxygen gas is suitable. In addition to oxygen gas, an inert gas such as He and Ar, and CO, $CO_2$, $NH_3$, $SO_2$, $N_2$, $NO_2$, and $H_2$ gases can also be added. The gas etching can also be performed not using oxygen gas but using only CO, $CO_2$, $NH_3$, $N_2$, $NO_2$, and $H_2$ gases. In particular, the latter gases are preferably used for protecting a side wall for preventing a pattern side wall from being undercut.

On the other hand, also in the etching of the intermediate layer in a three-layer process, gas etching is preferably used. As the gas etching, the same one as the one described in a two-layer process can be applied. In particular, the intermediate layer is preferably processed in a three-layer process using a fluorocarbon gas with the resist pattern as a mask. Thereafter, as described above, the intermediate layer pattern is used as a mask to perform, for example, oxygen gas etching, thereby processing the film for lithography.

Herein, in the case where an inorganic hard mask intermediate layer film is formed as the intermediate layer, a silicon oxide film, a silicon nitride film, and a silicon oxynitride film (SiON film) are formed by the CVD method, the ALD method, and the like. The nitride film forming method that can be used is, but not limited to the following, any method described in, for example, Japanese Patent Laid-Open No. 2002-334869 (Patent Literature 6) and WO2004/066377 (Patent Literature 7). While the photoresist film can be directly formed on such an intermediate layer film, an organic antireflective film (BARC) may also be formed on the intermediate layer film by spin coating, and the photoresist film may also be formed thereon.

As the intermediate layer, a polysilsesquioxane-based intermediate layer is also preferably used. The resist intermediate layer film is allowed to have an effect as an antireflective film, and thus tends to make it possible to effectively suppress reflection. A specific material for the polysilsesquioxane-based intermediate layer that can be used is, but not limited to the following, any material described in, for example, Japanese Patent Laid-Open No. 2007-226170 (Patent Literature 8) and Japanese Patent Laid-Open No. 2007-226204 (Patent Literature 9).

The next etching of the substrate can also be performed by an ordinary method, and, for example, when the substrate is made of $SiO_2$ or SiN, etching with mainly a fluorocarbon gas can be performed, and when the substrate is made of p-Si, Al, or W, etching mainly using a chlorine-based gas or bromine-based gas can be performed. In the case where the substrate is processed by the etching with a fluorocarbon gas, the silicon-containing resist in a two-layer resist process and the silicon-containing intermediate layer in a three-layer process are peeled off at the same time as the processing of the substrate. On the other hand, in the case where the substrate is processed by the etching with a chlorine-based gas or bromine-based gas, the silicon-containing resist layer or the silicon-containing intermediate layer is peeled off separately, and is generally peeled off by dry etching with a fluorocarbon gas after the substrate is processed.

The film for lithography of the present embodiment is characterized by being excellent in etching resistance of such a substrate. Herein, the substrate that can be used is appropriately selected from known ones, and is not particularly limited, but includes Si, α-Si, p-Si, $SiO_2$, SiN, SiON, W, TiN, and Al substrates. In addition, the substrate may also be a laminate having a processed film (processed substrate) on a base material (support). Such a processed film includes various Low-k films made of Si, $SiO_2$, SiON, SiN, p-Si, α-Si, W, W—Si, Al, Cu, and Al—Si, and stopper films thereof, and a material different from the base material (support) is usually used therefor. Herein, the thickness of the substrate to be processed or the processed film is not particularly limited, but it is usually preferably about 50 to 10,000 nm and more preferably 75 to 5,000 nm.

[Method for Purifying Material for Forming Film for Lithography]

A method for purifying the material for forming a film for lithography of the present embodiment comprises a step of bringing the solution (A) comprising the organic solvent optionally immiscible with water, and the material for forming an underlayer film for lithography into contact with an acidic aqueous solution for extraction. More specifically, in the present embodiment, the compound or the resin to be used in the present embodiment can be purified by dissolving the compound or the resin in the organic solvent optionally immiscible with water, bringing the solution into contact with an acidic aqueous solution for performing an extraction treatment, to thereby transfer a metal content included in the solution (A) including the compound or the resin and the organic solvent to an aqueous phase, and then separating an organic phase and the aqueous phase. The purification method of the material for forming a film for lithography of the present embodiment can allow the contents of various metals in the material for forming a film for lithography of the present embodiment to be remarkably reduced.

In the present embodiment, the organic solvent optionally immiscible with water means an organic solvent whose solubility in water at room temperature is less than 30%. Herein, the solubility is preferably less than 20%, more preferably less than 10%. The organic solvent optionally immiscible with water to be used in the present embodiment is not particularly limited, but it is preferably an organic solvent that can be safely applied to a semiconductor manufacturing process. The amount of the organic solvent to be used is usually about 1 to 100 times the amount of the compound or the resin to be used.

Specific examples of the solvent to be used include, but not limited to the following, ethers such as diethyl ether and diisopropyl ether, esters such as ethyl acetate, n-butyl acetate and isoamyl acetate, ketones such as methyl ethyl ketone, methyl isobutyl ketone, ethyl isobutyl ketone, cyclohexanone, cyclopentanone, 2-heptanone and 2-pentanone, glycol ether acetates such as ethylene glycol monoethyl ether acetate, ethylene glycol monobutyl ether acetate, propylene glycol monomethyl ether acetate (PGMEA) and propylene glycol monoethyl ether acetate, aliphatic hydrocarbons such as n-hexane and n-heptane, aromatic hydrocarbons such as toluene and xylene, and halogenated hydrocarbons such as methylene chloride and chloroform. Among them, toluene, 2-heptanone, cyclohexanone, cyclopentanone, methyl isobutyl ketone, propylene glycol monomethyl ether acetate, ethyl acetate, and the like are preferable, and cyclohexanone and propylene glycol monomethyl ether acetate are more preferable. These solvents can be used singly or as a mixture of two or more thereof.

The acidic aqueous solution to be used in the present embodiment is appropriately selected from aqueous solutions in which an organic or inorganic compound commonly known is dissolved in water. Examples include an aqueous solution in which a mineral acid such as hydrochloric acid, sulfuric acid, nitric acid or phosphoric acid is dissolved in water, or an aqueous solution in which an organic acid such as acetic acid, propionic acid, oxalic acid, malonic acid, succinic acid, fumaric acid, maleic acid, tartaric acid, citric acid, methanesulfonic acid, phenolsulfonic acid, p-toluenesulfonic acid or trifluoroacetic acid is dissolved in water. These acidic aqueous solutions can be used singly or in combinations of two or more thereof. Among these acidic aqueous solutions, an aqueous solution of sulfuric acid, nitric acid, or a carboxylic acid such as acetic acid, oxalic acid, tartaric acid or citric acid is preferable, an aqueous solution of sulfuric acid, oxalic acid, tartaric acid or citric acid is more preferable, and an aqueous solution of oxalic acid is further preferable. It is considered that a polyvalent carboxylic acid such as oxalic acid, tartaric acid and citric acid is coordinated with a metal ion to exert a chelating effect, and therefore tends to allow a metal to be more effectively removed. In addition, the water to be here used is preferably water having a low metal content according to the purpose of the present embodiment, such as ion-exchange water.

The pH of the acidic aqueous solution to be used in the present embodiment is not particularly limited, but the acidity of the aqueous solution is preferably adjusted in consideration of the effect on the compound or the resin to be used. The pH is usually in the range from about 0 to 5, preferably about 0 to 3.

The amount of the acidic aqueous solution to be used in the present embodiment is not particularly limited, but the amount to be used is preferably adjusted from the viewpoint of reducing the number of extractions for metal removal and the viewpoint of ensuring operation property in consideration of the total amount of the liquid. The amount of the aqueous solution to be used is usually 10 to 200% by mass, preferably 20 to 100% by mass, relative to the solution of the compound or the resin to be used.

In the present embodiment, the acidic aqueous solution described above can be brought into contact with the solution (A) including the material for forming an underlayer film (the compound or the resin) and the organic solvent optionally immiscible with water, to thereby extract the metal content.

The temperature in performing of the extraction treatment is usually in the range from 20 to 90° C., preferably 30 to 80° C. The extraction operation is performed by, for example, well mixing with stirring or the like and thereafter standing. Thus, the metal content included in the solution including the compound or the resin to be used and the organic solvent is transferred to the aqueous phase. In addition, the operation can allow the acidity of the solution to be reduced, suppressing the change of properties of the compound or the resin to be used.

The resulting mixture is separated to the solution phase including the compound or the resin to be used and the organic solvent, and the aqueous phase, and therefore the solution including the organic solvent is recovered by decantation or the like. The standing time is not particularly limited, but the standing time is preferably adjusted from the viewpoint of providing better separation to the solution phase including the organic solvent, and the aqueous phase. The standing time is usually 1 minute or more, preferably 10 minutes or more, more preferably 30 minutes or more. In addition, the extraction treatment may be performed only once, but is also effectively performed with operations such as mixing, standing and separation being repeatedly performed multiple times.

In the present embodiment, a step of performing an extraction treatment with water is preferably further included after the step of bringing the solution (A) into contact with the acidic aqueous solution for extraction. That is, preferably, the extraction treatment is performed by using the acidic aqueous solution, thereafter the solution (A) extracted and recovered from the aqueous solution is preferably further subjected to the extraction treatment with water. The extraction treatment with water is performed by, for example, well mixing with stirring or the like and thereafter standing. The resulting solution is separated to the solution phase including the compound or the resin and the organic solvent, and the aqueous phase, and therefore the solution phase is recovered by decantation or the like. In addition, the water to be here used is preferably water having a low metal content according to the purpose of the present embodiment, such as ion-exchange water. The extraction treatment may be performed only once, but is also effectively performed with operations such as mixing, standing and separation being repeatedly performed multiple times. In addition, conditions in the extraction treatment, such as the ratio of both to be used, the temperature and the time, are not particularly limited, but may be the same as in the case of the contact treatment with the acidic aqueous solution above.

The water content that can be incorporated in the solution thus obtained, including the compound or the resin and the organic solvent, can be easily removed by performing an operation such as distillation under reduced pressure. In addition, an organic solvent can be if necessary added to adjust the concentration of the compound or the resin to any concentration.

The method of isolating the compound or the resin from the resulting solution including the organic solvent can be performed by a known method such as removal under reduced pressure, separation by reprecipitation and a combination thereof. If necessary, a known treatment such as a concentration operation, a filtration operation, a centrifugation operation and a drying operation can be further performed.

EXAMPLES

Hereinafter, the present embodiment will be described by Synthesis Examples and Examples in more detail, but the present embodiment is not limited thereto at all.

[Carbon Concentration and Oxygen Concentration]

The carbon concentration and the oxygen concentration (% by mass) were measured by organic element analysis.

Apparatus: CHN CORDER MT-6 (manufactured by Yanaco Bunseki Kogyo Co.)

[Molecular Weight]

Measurement was performed by LC-MS analysis using Acquity UPLC/MALDI-Synapt HDMS manufactured by Water.

[Molecular Weight in Terms of Polystyrene]

Gel permeation chromatography (GPC) analysis was used to determine the weight average molecular weight (Mw) and the number average molecular weight (Mn) in terms of polystyrene, and to determine the degree of dispersion (Mw/Mn).

Apparatus: Shodex GPC-101 type (manufactured by Showa Denko K. K.)

Column: KF-80M×3

Eluent: THF 1 mL/min

Temperature: 40° C.

[Pyrolysis Temperature (Tg)]

An EXSTAR 6000 DSC apparatus manufactured by SII NanoTechnology Inc. was used, and about 5 mg of a sample was placed in an unsealed aluminum container and heated to 500° C. at a rate of temperature rise of 10° C./min in a nitrogen gas (30 mL/min) stream. In this time, a temperature at which a reducing portion appeared on the base line was defined as a pyrolysis temperature (Tg).

[Solubility]

The amount of each compound dissolved in 1-methoxy-2-propanol (PGME), propylene glycol monomethyl ether acetate (PGMEA), cyclopentanone (CPN), and cyclohexanone (CHN) was measured at 23° C., and the results were evaluated according to the following criteria.

Evaluation A: 10% by mass or more

Evaluation B: less than 10% by mass

Synthesis Example 1 Synthesis of Dibenzochrysene (DBC)

On the basis of the description of Example 1 in Japanese Patent Laid-Open No. 2013-227307, 6.8 g of dibenzo[g,p]chrysene (DBC) was obtained as a brown powdery solid by synthesis. As a result of liquid chromatography analysis, the obtained solid had a purity of 99.8%.

As a result of thermogravimetric measurement (TG), the 15% thermal weight loss temperature of the resulting compound (DBC) was 400° C. or higher. Therefore, the compound was evaluated to have a high heat resistance and be applicable to high-temperature baking.

As a result of evaluation of the solubility in CPN and CHN, the solubility was 10% by mass or more (Evaluation A) and compound (DBC) was evaluated to have an excellent solubility. Therefore, compound (DBC) was evaluated to have a high storage stability in a solution state and also be sufficiently applicable to CPN and CHN used in washing and/or as a solvent in a semiconductor microfabrication process.

Synthesis Example 2 Synthesis of Hydroxydibenzochrysene (HDBC)

On the basis of the description of Example 7 in Japanese Patent Laid-Open No. 2013-227307, 1.6 g of hydroxydibenzochrysene (HDBC) was obtained as a brown powdery solid by the sulfonation of dibenzo[g,p]chrysene on the same scale, followed by the hydroxylation of the obtained dibenzo[g,p]chrysene sulfonate.

As a result of liquid chromatography mass spectrometry (LC/MS analysis), 98% of the obtained compound was 4-substituted hydroxydibenzochrysene (HDBC-4), and the remaining portion was 3-substituted hydroxydibenzochrysene (HDBC-3).

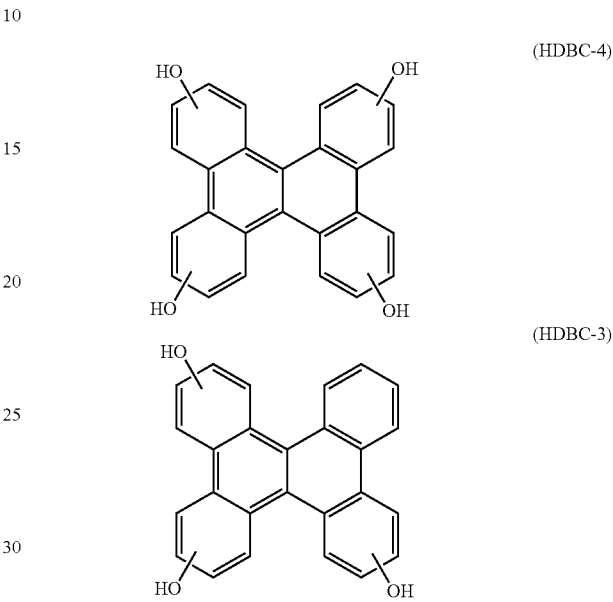

As a result of thermogravimetric measurement (TG), the 15% thermal weight loss temperature of the resulting compound (HDBC) was 400° C. or higher. Therefore, the compound was evaluated to have a high heat resistance and be applicable to high-temperature baking.

As a result of evaluation of the solubility in PGME and PGMEA, the solubility was 10% by mass or more (Evaluation A) and compound (HDBC) was evaluated to have an excellent solubility. Therefore, compound (HDBC) was evaluated to have a high storage stability in a solution state and also be sufficiently applicable to an edge bead rinse liquid (mixed liquid of PGME/PGMEA) widely used in a semiconductor microfabrication process.

Synthesis Example 3 Synthesis of R-DBC

A container (internal capacity: 100 mL) equipped with a stirrer, a condenser tube, and a burette was charged with 10 g (30 mmol) of DBC, 0.7 g (42 mmol) of paraformaldehyde, 50 mL of glacial acetic acid, and 50 mL of PGME, and 8 mL of 95% sulfuric acid was added thereto. This reaction solution was stirred at 100° C. for 6 hours to perform reaction. Next, the reaction solution was concentrated. The reaction product was precipitated by the addition of 1000 ml of methanol. After cooling to room temperature, the precipitates were separated by filtration. The obtained solid matter was filtered, dried, and then separated and purified by column chromatography to obtain 6.4 g of the objective resin (R-DBC).

As a result of measuring the polystyrene based molecular weight of the obtained resin by the above method, it was Mn: 698, Mw: 1563, and Mw/Mn: 2.24.

As a result of thermogravimetric measurement (TG), the 15% thermal weight loss temperature of the resulting resin (R-DBC) was 400° C. or higher. The resin was evaluated to have a high heat resistance and be applicable to high-temperature baking.

The solubility in PGME and PGMEA was as good as 10% by mass or more (Evaluation A). Therefore, resin (R-DBC) was evaluated to have a high storage stability in a solution state and also be sufficiently applicable to an edge bead rinse liquid (mixed liquid of PGME/PGMEA) widely used in a semiconductor microfabrication process.

Production Example 1

A four-neck flask having a bottom outlet and an inner volume of 10 L, equipped with a Dimroth condenser, a thermometer and a stirring blade was prepared. To this four-neck flask were charged 1.09 kg (7 mol, produced by Mitsubishi Gas Chemical Company, Inc.) of 1,5-dimethylnaphthalene, 2.1 kg (28 mol as formaldehyde, produced by Mitsubishi Gas Chemical Company, Inc.) of a 40% by mass aqueous formalin solution and 0.97 mL of 98% by mass sulfuric acid (produced by Kanto Chemical Co., Inc.) under a nitrogen stream, and allowed the reaction to run under ordinary pressure for 7 hours with refluxing at 100° C. Thereafter, ethylbenzene (special grade chemical, produced by Wako Pure Chemical Industries, Ltd.) (1.8 kg) as a dilution solvent was added to the reaction solution and left to stand, and then an aqueous phase being a bottom phase was removed. Furthermore, the resultant was neutralized and washed with water, and ethylbenzene and the unreacted 1,5-dimethylnaphthalene were distilled off under reduced pressure, thereby providing 1.25 kg of a dimethylnaphthalene formaldehyde resin as a light-brown solid.

With respect to the molecular weight of the resulting dimethylnaphthalene formaldehyde resin, Mn was 562, Mw was 1168 and Mw/Mn was 2.08. In addition, the carbon concentration was 84.2% by mass, and the oxygen concentration was 8.3% by mass.

Subsequently, a four-neck flask having an inner volume of 0.5 L, equipped with a Dimroth condenser, a thermometer and a stirring blade, was prepared. To this four-neck flask were charged 100 g (0.51 mol) of the dimethylnaphthalene formaldehyde resin obtained as described above and 0.05 g of paratoluenesulfonic acid under a nitrogen stream, heated for 2 hours with the temperature being raised to 190° C., and then stirred. Thereafter, 52.0 g (0.36 mol) of 1-naphthol was further added thereto, and further heated to 220° C. to allow the reaction to run for 2 hours. After being diluted with a solvent, the resultant was neutralized and washed with water, and the solvent was removed under reduced pressure to thereby provide 126.1 g of a modified resin (CR-1) as a blackish brown solid.

With respect to the resulting resin (CR-1), Mn was 885, Mw was 2220 and Mw/Mn was 4.17. In addition, the carbon concentration was 89.1% by mass and the oxygen concentration was 4.5% by mass.

The solubility in PGME and PGMEA was as good as 10% by mass or more (Evaluation A). Therefore, resin (R-DBC) was evaluated to have a high storage stability in a solution state and also be sufficiently applicable to an edge bead rinse liquid (mixed liquid of PGME/PGMEA) widely used in a semiconductor microfabrication process.

Synthesis Example 4 Synthesis of Iodododibenzochrysene

On the basis of the description of Japanese Patent Laid-Open No. 2013-227307, a four necked flask (capacity: 5 L) equipped with a mechanical stirring apparatus and a reflux condenser tube was charged with 30 g (0.0913 mol) of DBC obtained in Synthesis Example 1 and 900 g of chloroform (manufactured by Wako Pure Chemical Industries, Ltd.), and DBC was dissolved in chloroform by stirring at room temperature. The flask was cooled to 2° C. using an ice salt bath (−5° C.). In this state, 950 g of a 5% solution of $I_2$ in $CHCl_3$ (solution of iodine in chloroform) was dropped thereto over 1 hour using a dropping pump (PTFE diaphragm pump). While the stirring was continued, the reaction was monitored by HPLC analysis every 1 hour after the dropping terminated. The reaction was stopped by the addition of 620 g of a 1 N aqueous $NaHSO_3$ solution (1 mol/L aqueous $NaHSO_3$ solution). Then, the contents were neutralized by the addition of 526.6 g of a 9% aqueous $NaHCO_3$ solution, and the obtained contents were washed with water three times. Subsequently, the solvent was removed from this organic phase by concentration under reduced pressure using an evaporator to obtain 41.2 g of a white solid. As a result of liquid chromatography mass spectrometry (LC/MS analysis), the obtained compound was an iododibenzochrysene mixture containing 7.0% monoiododibenzochrysene (IDBC-1), 80% diiododibenzochrysene (IDBC-2), and 13% triiododibenzochrysene (IDBC-3).

The solubility in PGME and PGMEA was as good as 10% by mass or more (Evaluation A). Therefore, resin (R-DBC) was evaluated to have a high storage stability in a solution state and also be sufficiently applicable to an edge bead rinse liquid (mixed liquid of PGME/PGMEA) widely used in a semiconductor microfabrication process.

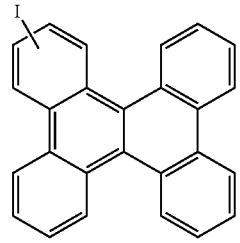

(IDBC-1)

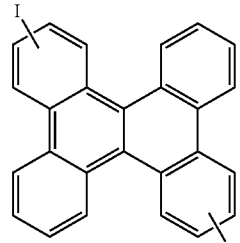

(IDBC-2)

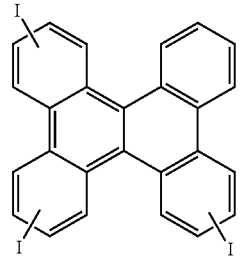

(IDBC-3)

Synthesis Example 5 Synthesis of Dinitrodibenzochrysene

On the basis of the description of Japanese Patent Laid-Open No. 2013-227307, a four necked flask (capacity: 300 mL) equipped with a mechanical stirring apparatus and a reflux condenser tube was charged with 6.67 g (0.0203 mol) of DBC obtained in Synthesis Example 1 and 200 g of chloroform (manufactured by Wako Pure Chemical Industries, Ltd.), and DBC was dissolved in chloroform by stirring in a water bath (26° C.). Then, 7.58 g of a 67.5% aqueous $HNO_3$ solution (aqueous nitric acid solution) (containing 0.0812 mol of $HNO_3$) was dropped thereto over 5 minutes using a pipette. This dropping caused heat generation of the contents so that the temperature of the solution was elevated to 28° C. In addition, the color of the solution was changed from pale yellow color to dark brown color in about 10 minutes from the completion of the dropping. The stirring was continued in a state where the temperature of the contents was 26 to 27° C. A yellow orange solid started to be precipitated about 15 minutes after the dropping terminated. The precipitates were increased while the time passed. The contents were in a slurry form in 2 hours from the completion of the dropping. Subsequently, the water bath was changed to a hot water bath having a temperature of 65° C., and reflux reaction (internal temperature: 59° C.) was performed for 4 hours. In the contents, yellow slurry particles were rendered finer while the ratio of dinitrodibenzochrysene (NO2DBC-2) detected by LCMS analysis was increased, and the progression of its production was confirmed.

In order to promote the production of dinitrodibenzochrysene, 1.89 g of a 67.5% aqueous $HNO_3$ solution (aqueous nitric acid solution) (containing 0.0203 mol of $HNO_3$) was further added thereto, and the reflux reaction was continued for 1 hour to complete the reaction. Subsequently, the contents after the above operation were cooled with stirring until the temperature reached 25° C. Then, solid liquid separation was performed using a Buchner funnel and a Kiriyama filter paper to isolate solid matter. Subsequently, the obtained solid matter was washed with 50 g of methanol for the purpose of removing acid portions therefrom, and then dried under reduced pressure at a temperature of 60° C. for 12 hours to obtain 6 g of a yellow powder. As a result of liquid chromatography mass spectrometry (LC/MS analysis), the above yellow powder was confirmed to be dinitrodibenzochrysene (NO2DBC-2) containing 2.0% mononitrodibenzochrysene (NO2DBC-1).

The solubility in PGME and PGMEA was as good as 10% by mass or more (Evaluation A). Therefore, resin (R-DBC) was evaluated to have a high storage stability in a solution state and also be sufficiently applicable to an edge bead rinse liquid (mixed liquid of PGME/PGMEA) widely used in a semiconductor microfabrication process.

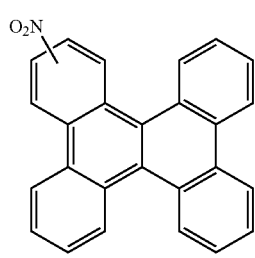

(NO2DBC-1)

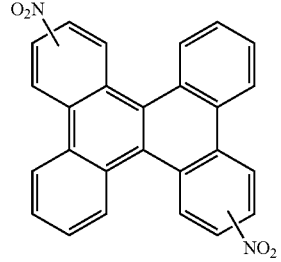

(NO2DBC-2)

Synthesis Example 6 Synthesis of Diaminodibenzochrysene

On the basis of the description of Japanese Patent Laid-Open No. 2013-227307, a three necked flask (capacity: 200 mL) equipped with a magnet type stirring apparatus and a reflux condenser tube was charged with 2.0 g of the above mixture of nitrodibenzochrysene obtained in Synthesis Example 5, 0.2 g (dry mass based) of 5% Pd/C (50% water wetted palladium carbon), and 30 g of tetrahydrofuran (THF), and the contents were heated to 60° C. by stirring in a hot water bath (65° C.). Subsequently, 2.39 g of an 80% aqueous hydrazine solution, i.e., an aqueous solution containing 0.0382 mol of hydrazine ($NH_2NH_2$), was dropped thereto over 5 minutes using a pipette. This dropping gradually changed the contents from a yellow slurry state to a red brown liquid. In this operation, the generation of nitrogen gas and heat generation (reflux) were observed. Then, the reflux was continued with stirring for 2 hours in a state where the temperature of the contents was 63° C. to complete the reaction. Then, for the purpose of removing Pd/C, solid liquid separation was performed at a temperature of about 30° C. using a Buchner funnel, No. 5C filter paper, and RADIOLITE (filter aid) to isolate a red brown liquid. Subsequently, this red brown solution was charged to a three necked flask (capacity: 100 mL) equipped with a concentration apparatus, and the volume was decreased under reduced pressure using an aspirator at an internal temperature of about 45° C. until the amount of the solution (tetrahydrofuran) was almost halved to obtain a concentrated red brown solution. The red brown solution thus obtained was further dropped using a pipette to 120 g of distilled water stirred in a beaker (capacity: 300 mL) at room temperature. This dropping precipitated yellow red solid matter. The contents were subjected to solid liquid separation using a Buchner funnel and a Kiriyama filter paper to obtain yellow orange solid matter. The obtained solid matter was dried at a temperature of 60° C. and under reduced pressure of 10 mmHg for 12 hours to obtain 1.4 g of a yellow orange powder. As a result of liquid chromatography mass spectrometry (LC/MS analysis), the above yellow orange powder was confirmed to be diaminodibenzochrysene (NH2DBC-2) containing 4.0% monoaminodibenzochrysene (NH2DBC-1).

The solubility in PGME and PGMEA was as good as 10% by mass or more (Evaluation A). Therefore, resin (R-DBC) was evaluated to have a high storage stability in a solution state and also be sufficiently applicable to an edge bead rinse liquid (mixed liquid of PGME/PGMEA) widely used in a semiconductor microfabrication process.

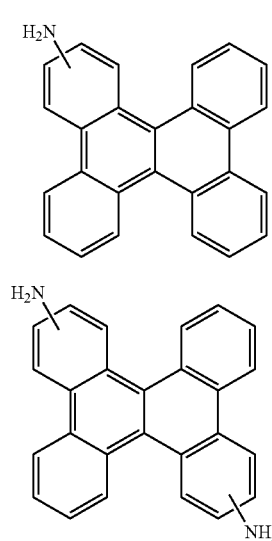

(NH2DBC-1)

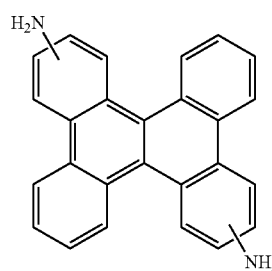

(NH2DBC-2)

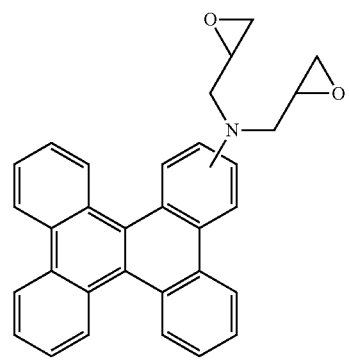

(AGDBC-1)

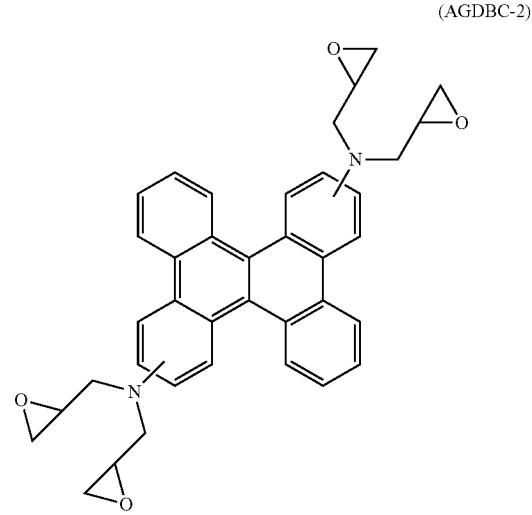

(AGDBC-2)

Synthesis Example 7 Synthesis of Aminodiglycidyl Dibenzochrysene

On the basis of the description of Japanese Patent Laid-Open No. 2013-227307, a four necked flask (capacity: 300 mL) equipped with a magnet type stirring apparatus and a reflux condenser tube was charged with 10.85 g of the mixture of aminodibenzochrysene obtained in Synthesis Example 6, 27 g of ethanol (manufactured by Wako Pure Chemical Industries, Ltd.), and 67.2 g (0.726 mol) of epichlorohydrin (manufactured by Kanto Chemical Co., Inc.), and the contents were reacted with stirring at an internal temperature of 80° C. for 6 hours while incubated using a hot water bath. This changed the contents to a red brown solution. Subsequently, while the stirring was continued in a hot water bath, the internal temperature was lowered to 60° C. Then, 10.67 g of a 50% aqueous NaOH solution (aqueous sodium hydroxide solution) (containing 0.267 mol of NaOH) was dropped thereto over 5 hours using a pipette. Then, the stirring was continued for 3 hours and stopped. Subsequently, the solvent (ethanol+water) was removed under reduced pressure using an aspirator. Then, the contents were dissolved by the addition of 100 g of toluene, and washed with 50 g of distilled water three times. The solvent in the organic phase thus washed with water was removed at a temperature of 100° C. and under reduced pressure of 1 mmHg to obtain 12.3 g of a red brown mass. As a result of liquid chromatography mass spectrometry (LC/MS analysis), the above yellow orange powder was confirmed to be diaminodiglycidyl dibenzochrysene (AGDBC-2) containing 4.0% monoaminodiglycidyl dibenzochrysene (AGDBC-1).

The solubility in PGME and PGMEA was as good as 10% by mass or more (Evaluation A). Therefore, resin (R-DBC) was evaluated to have a high storage stability in a solution state and also be sufficiently applicable to an edge bead rinse liquid (mixed liquid of PGME/PGMEA) widely used in a semiconductor microfabrication process.

Synthesis Example 8 Synthesis of Dibenzochrysene Glycidyl Ether

On the basis of the description of Japanese Patent Laid-Open No. 2014-152164, 10 g (about 0.255 mol) of hydroxydibenzochrysene obtained in Synthesis Example 2, 100 g of ethanol, and 300 g (3.24 mol) of epichlorohydrin (manufactured by Kanto Chemical Co., Inc.) were charged, and stirred and mixed at 40° C. While the internal temperature was kept at 40° C., 4.3 g (0.11 mol) of a sodium hydroxide powder was added to the above contents to obtain a solution. Then, the solvent (ethanol and epichlorohydrin) was removed under reduced pressure. Subsequently, 100 g of methyl isobutyl ketone (MIBK) was added to the contents thus free from the solvent, and the mixture was stirred. Then, insoluble matter was removed to obtain 1.2 g of dibenzochrysene glycidyl ether (DBCGE) as yellow oily matter. As a result of liquid chromatography mass spectrometry (LC/MS analysis), the obtained compound was confirmed to be 4-substituted dibenzochrysene glycidyl ether (DBCGE-4) containing 2.0% 3-substituted dibenzochrysene glycidyl ether (DBCGE-3) represented by the following formula:

(DBCGE-3)

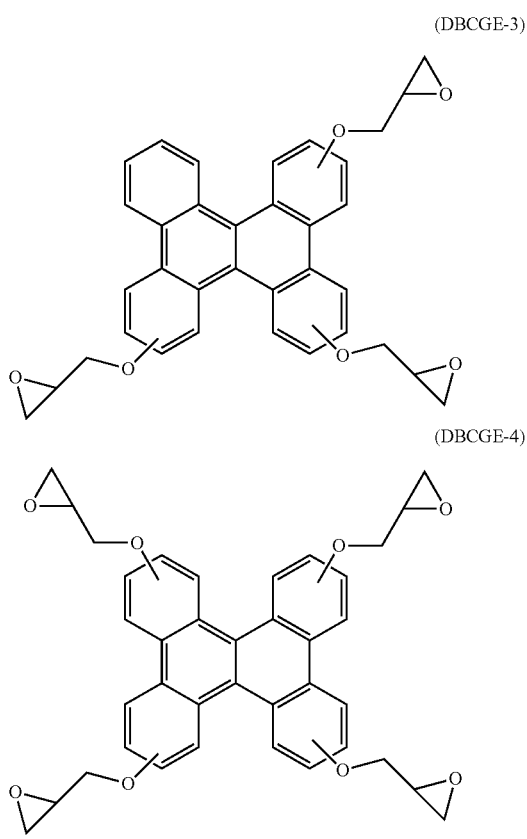

(DBCGE-4)

(ACDBC-4)

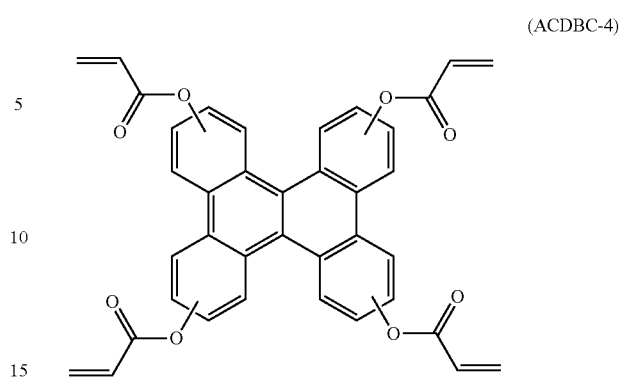

The solubility in PGME and PGMEA was as good as 10% by mass or more (Evaluation A). Therefore, resin (R-DBC) was evaluated to have a high storage stability in a solution state and also be sufficiently applicable to an edge bead rinse liquid (mixed liquid of PGME/PGMEA) widely used in a semiconductor microfabrication process.

Synthesis Example 10 Synthesis of Dibenzochrysene Methacryl Compound

On the basis of the description of Japanese Patent Laid-Open No. 2014-152164, 10 g (0.026 mol) of hydroxydibenzochrysene obtained in Synthesis Example 2, and 50 mg of phenothiazine (Kanto Chemical Co., Inc.) were dissolved in 200 g of acetonitrile (manufactured by Wako Pure Chemical Industries, Ltd.). Then, 20.9 g (0.2 mol) of methacryloyl chloride (manufactured by Wako Pure Chemical Industries, Ltd.) and 26 g (0.26 mol) of triethylamine (manufactured by Kanto Chemical Co., Inc.) were dropped thereto, and the mixture was stirred at 25° C. for 6 hours. Then, 10 g of methanol was dropped thereto. The obtained reaction solution was washed by the addition of 800 g of ethyl acetate and 150 g of distilled water. Washing with distilled water was repeated twice. Then, the solvent was distilled off under reduced pressure using an evaporator. The obtained oily matter was purified by silica gel column chromatography using a mixed solvent of toluene/ethyl acetate=10/1 and dried under reduced pressure to obtain 11.3 g of a brown powdery solid. As a result of liquid chromatography mass spectrometry (LC/MS analysis), the obtained compound was confirmed to be a 4-substituted dibenzochrysene methacryl compound (MCDBC-4) represented by the following formula:

(MCDBC-4)

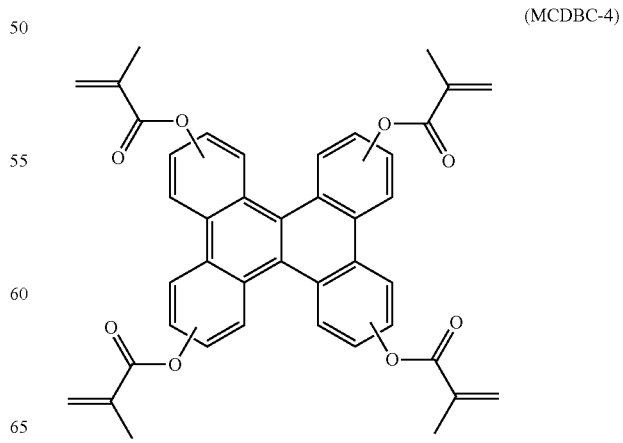

The solubility in PGME and PGMEA was as good as 10% by mass or more (Evaluation A). Therefore, resin (R-DBC) was evaluated to have a high storage stability in a solution state and also be sufficiently applicable to an edge bead rinse liquid (mixed liquid of PGME/PGMEA) widely used in a semiconductor microfabrication process.

Synthesis Example 9 Synthesis of Dibenzochrysene Acryl Compound

On the basis of the description of Japanese Patent Laid-Open No. 2014-152164, 10 g (0.026 mol) of hydroxydibenzochrysene obtained in Synthesis Example 2, and 50 mg of phenothiazine (Kanto Chemical Co., Inc.) were dissolved in 200 g of acetonitrile (manufactured by Wako Pure Chemical Industries, Ltd.). Then, 18.5 g (0.2 mol) of acryloyl chloride (manufactured by Wako Pure Chemical Industries, Ltd.) and 26 g (0.26 mol) of triethylamine (manufactured by Kanto Chemical Co., Inc.) were dropped thereto, and the mixture was stirred at 25° C. for 6 hours. Then, 10 g of methanol was dropped thereto. The reaction solution was washed by the addition of 800 g of ethyl acetate and 150 g of distilled water. Washing with distilled water was repeated twice. Then, the solvent was distilled off under reduced pressure using an evaporator. The obtained oily matter was purified by silica gel column chromatography using a mixed solvent of toluene/ethyl acetate=10/1 and dried under reduced pressure to obtain 9.4 g of a brown powdery solid. As a result of liquid chromatography mass spectrometry (LC/MS analysis), the obtained compound was confirmed to be a 4-substituted dibenzochrysene acryl compound (ACDBC-4) represented by the following formula:

The solubility in PGME and PGMEA was as good as 10% by mass or more (Evaluation A). Therefore, resin (R-DBC) was evaluated to have a high storage stability in a solution state and also be sufficiently applicable to an edge bead rinse liquid (mixed liquid of PGME/PGMEA) widely used in a semiconductor microfabrication process.

Synthesis Example 11 Synthesis of Acryloyloxydibenzochrysene Compound

On the basis of the description of Japanese Patent Laid-Open No. 2014-152164, 5.0 g (0.0081 mol) of dibenzochrysene glycidyl ether obtained in Synthesis Example 8, 30 mg of phenothiazine (Kanto Chemical Co., Inc.), and 60 mg of triphenylphosphine (manufactured by Wako Pure Chemical Industries, Ltd.) were dissolved in 50.0 g (0.7 mol) of acrylic acid (manufactured by Kanto Chemical Co., Inc.). Then, 100 g of toluene (manufactured by Wako Pure Chemical Industries, Ltd.) was added thereto, and the mixture was reacted at 90° C. for 10 hours in an oil bath. 400 g of ethyl acetate and a saturated aqueous solution of sodium bicarbonate were added to the obtained reaction solution, followed by the separation of the ethyl acetate phase. Subsequently, insoluble matter was filtered off, and the ethyl acetate phase was then washed with 100 g of distilled water, further concentrated under reduced pressure, and then dried to obtain 3.1 g of a brown solid. As a result of liquid chromatography mass spectrometry (LC/MS analysis), the obtained compound was confirmed to be a mixture of acryloyloxydibenzochrysene (AODBC) represented by the following formulas:

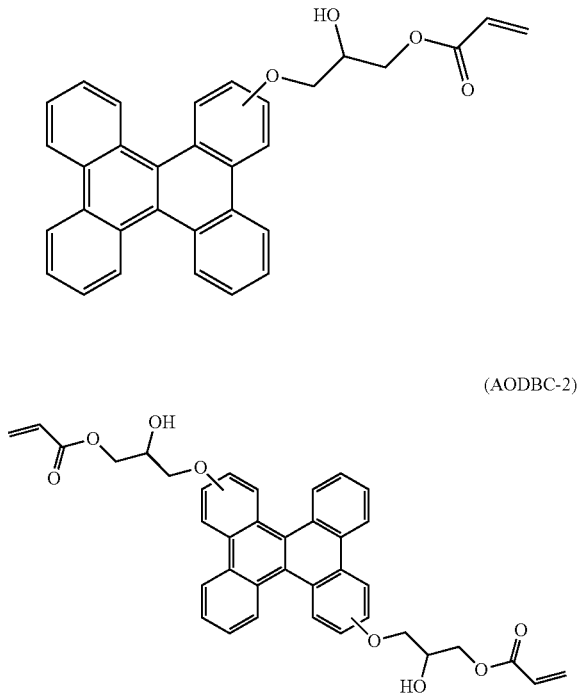

(AODBC-1)

(AODBC-2)

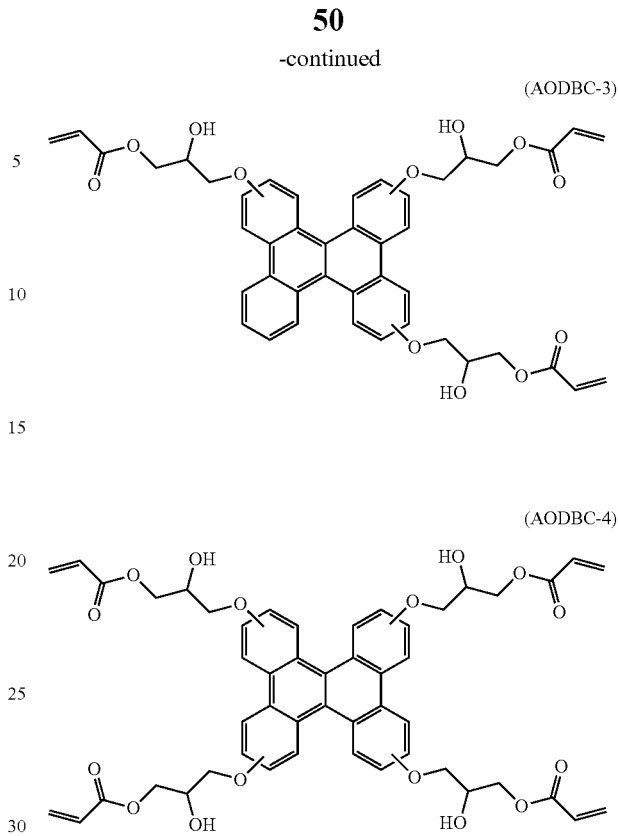

(AODBC-3)

(AODBC-4)

The solubility in PGME and PGMEA was as good as 10% by mass or more (Evaluation A). Therefore, resin (R-DBC) was evaluated to have a high storage stability in a solution state and also be sufficiently applicable to an edge bead rinse liquid (mixed liquid of PGME/PGMEA) widely used in a semiconductor microfabrication process.

Synthesis Example 12 Synthesis of Methacryloyloxydibenzochrysene Compound

On the basis of the description of Japanese Patent Laid-Open No. 2014-152164, 5.0 g (0.0081 mol) of dibenzochrysene glycidyl ether obtained in Synthesis Example 8, 30 mg of phenothiazine (Kanto Chemical Co., Inc.), and 60 mg of triphenylphosphine (manufactured by Wako Pure Chemical Industries, Ltd.) were dissolved in 60.3 g (0.7 mol) of methacrylic acid (manufactured by Wako Pure Chemical Industries, Ltd.). Then, 100 g of toluene (manufactured by Wako Pure Chemical Industries, Ltd.) was added thereto. The mixture was reacted at 90° C. for 10 hours in an oil bath. 400 g of ethyl acetate and a saturated aqueous solution of sodium bicarbonate were added to the obtained reaction solution, followed by the separation of the ethyl acetate phase. Subsequently, insoluble matter was filtered off, and the ethyl acetate phase was then washed with 100 g of distilled water, concentrated under reduced pressure, and then dried to obtain 3.6 g of a brown solid. As a result of liquid chromatography mass spectrometry (LC/MS analysis), the obtained compound was confirmed to be a mixture of methacryloyloxydibenzochrysene (MAODBC) represented by the following formulas:

(MAODBC-1)

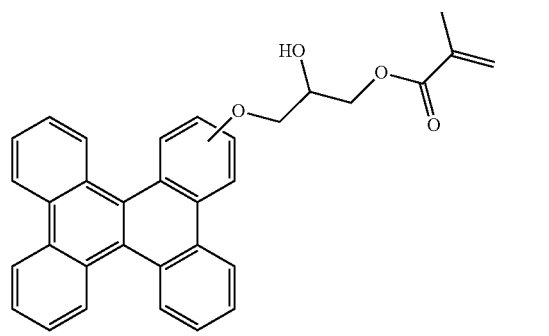

(MAODBC-2)

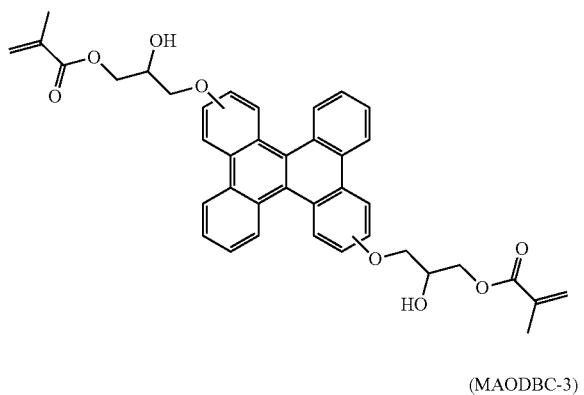

(MAODBC-3)

(MAODBC-4)

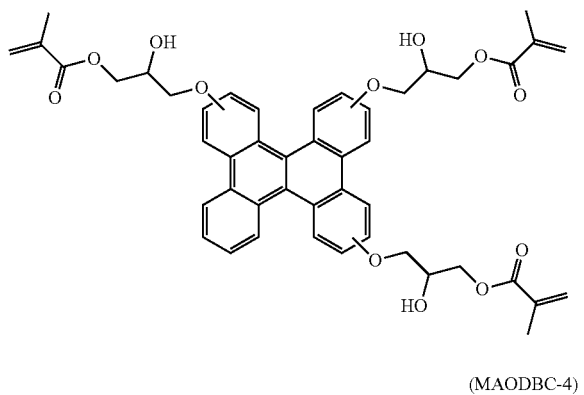

The solubility in PGME and PGMEA was as good as 10% by mass or more (Evaluation A). Therefore, resin (R-DBC) was evaluated to have a high storage stability in a solution state and also be sufficiently applicable to an edge bead rinse liquid (mixed liquid of PGME/PGMEA) widely used in a semiconductor microfabrication process.

Synthesis Example 13 Synthesis of Tetrathiol Dibenzochrysene

On the basis of the description of Japanese Patent Laid-Open No. 2013-227307, after sulfonation of dibenzochrysene, the sulfonic acid group of the obtained compound was converted to a sulfonyl halogen group (—SO$_2$X). The sulfonyl halogen group of the obtained compound was further converted to a thiol group to obtain 8.6 g of tetrathiol dibenzochrysene. As a result of liquid chromatography mass spectrometry (LC/MS analysis), the obtained compound was confirmed to be tetrathiol dibenzochrysene (SDBC-4) represented by the following formula:

(SDBC-4)

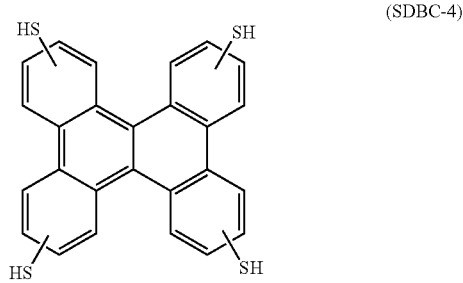

The solubility in PGME and PGMEA was as good as 10% by mass or more (Evaluation A). Therefore, resin (R-DBC) was evaluated to have a high storage stability in a solution state and also be sufficiently applicable to an edge bead rinse liquid (mixed liquid of PGME/PGMEA) widely used in a semiconductor microfabrication process.

Synthesis Example 14 Synthesis of Tetraallyloxydibenzochrysene

On the basis of the description of Japanese Patent Laid-Open No. 2014-152164, 5 g (0.013 mol) of hydroxydibenzochrysene obtained in Synthesis Example 2 and 12.3 g (0.10 mol) of allyl bromide (manufactured by Tokyo Chemical Industry Co., Ltd.) were dissolved in 50 g of dimethyl sulfoxide (manufactured by Wako Pure Chemical Industries, Ltd.). Then, 2.54 g (0.064 mol) of sodium hydroxide (manufactured by Tosoh Corporation, product name: Tosoh Pearl) was added thereto, and the mixture was stirred at 80° C. for 18 hours under a nitrogen gas stream. After the reaction terminated, the reaction solution was washed by the addition of 300 g of ethyl acetate and 80 g of distilled water. Washing with distilled water was repeated twice. Then, the solvent was distilled off under reduced pressure using an evaporator. The obtained solid was purified by silica gel column chromatography using toluene and dried under reduced pressure to obtain 4.6 g of a brown powdery solid. As a result of liquid chromatography mass spectrometry (LC/MS analysis), the obtained compound was confirmed to be tetraallyloxydibenzochrysene (TAODBC) represented by the following formula:

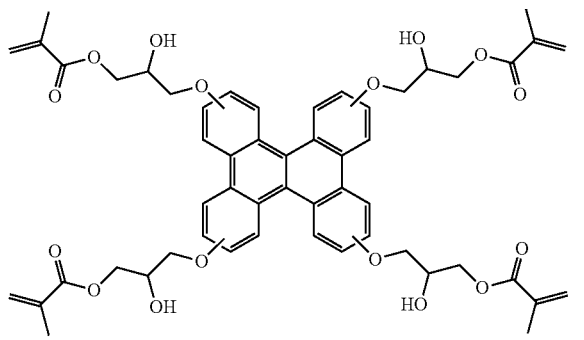

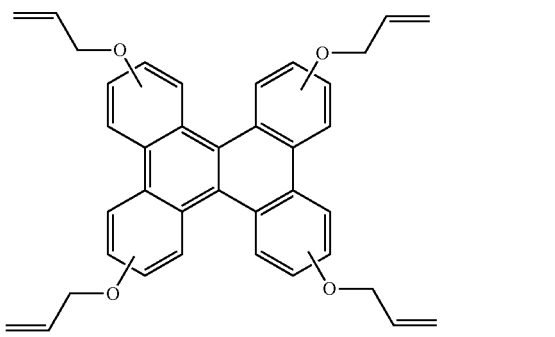
(TAODBC)

The solubility in PGME and PGMEA was as good as 10% by mass or more (Evaluation A). Therefore, resin (R-DBC) was evaluated to have a high storage stability in a solution state and also be sufficiently applicable to an edge bead rinse liquid (mixed liquid of PGME/PGMEA) widely used in a semiconductor microfabrication process.

Examples 1 to 14 and Comparative Example 1

A material for forming a film for lithography in each of Examples 1 to 14 and Comparative Example 1 was prepared using the compound or the resin obtained in each of Synthesis Examples 1 to 14 above, the resin obtained in Production Example 1 above, and the following materials so that each composition shown in Table 1 was achieved.

Acid generating agent: di-tert-butyldiphenyliodonium nonafluoromethanesulfonate (DTDPI) produced by Midori Kagaku Co., Ltd.

Crosslinking agent: Nikalac MX270 (Nikalac) produced by Sanwa Chemical Co., Ltd.

Organic solvent: propylene glycol monomethyl ether acetate (PGMEA)

Then, each composition for forming a film for lithography of Examples 1 to 14 and Comparative Example 1 was spin-coated on a silicon substrate, thereafter baked at 240° C. for 60 seconds and further at 400° C. for 120 seconds to prepare each underlayer film having a film thickness of 200 nm. Then, an etching test was performed under conditions shown below to evaluate etching resistance. The evaluation results are shown in Table 1.

[Etching Test]
Etching apparatus: RIE-10NR manufactured by Samco Inc.
Output: 50 W
Pressure: 20 Pa
Time: 2 min
Etching gas
Ar gas flow rate:$CF_4$ gas flow rate:$O_2$ gas flow rate=50:5:5 (sccm)

[Evaluation of Etching Resistance]
The evaluation of etching resistance was performed according to the following procedure.

First, an underlayer film of novolac was prepared under the same conditions as those in Examples 1 to 14 except that novolac (PSM4357 produced by Gunei Chemical Industry Co., Ltd.) was used instead of the compounds or the resin in Examples 1 to 14. Then, the etching test was performed with respect to the underlayer film of novolac as a subject, and the etching rate in that time was measured.

Then, the etching test was performed with respect to each underlayer film of Examples 1 to 14 and Comparative Example 1 as a subject, and the etching rate in that time was measured.

Then, the etching resistances were evaluated according to the following criteria based on the etching rate of the underlayer film of novolac.

<Evaluation Criteria>
A; etching rate of less than −10% compared with the underlayer film of novolac
B; etching rate of −10% to +5% compared with underlayer film of novolac
C; etching rate of more than +5% compared with the underlayer film of novolac

TABLE 1

| | Compound or Resin (parts by mass) | Organic solvent (parts by mass) | Acid generating agent (parts by mass) | Crosslinking agent (parts by mass) | Evaluation of etching resistance |
|---|---|---|---|---|---|
| Example 1 | DBC obtained in Synthesis Example 1 (10) | PGMEA (90) | DTDPI (0.5) | Nikalac (0.5) | A |
| Example 2 | HDBC mixture obtained in Synthesis Example 2 (10) | PGMEA (90) | DTDPI (0.5) | Nikalac (0.5) | A |
| Example 3 | R-DBC obtained in Synthesis Example 3 (10) | PGMEA (90) | DTDPI (0.5) | Nikalac (0.5) | A |
| Example 4 | IDBC mixture obtained in Synthesis Example 4 (10) | PGMEA (90) | DTDPI (0.5) | Nikalac (0.5) | A |
| Example 5 | NO2DBC mixture obtained in Synthesis Example 5 (10) | PGMEA (90) | DTDPI (0.5) | Nikalac (0.5) | A |
| Example 6 | NH2DBC mixture obtained in Synthesis Example 6 (10) | PGMEA (90) | DTDPI (0.5) | Nikalac (0.5) | A |
| Example 7 | AGDBC mixture obtained in Synthesis Example 7 (10) | PGMEA (90) | DTDPI (0.5) | Nikalac (0.5) | A |
| Example 8 | DBCGE mixture obtained in Synthesis Example 8 (10) | PGMEA (90) | DTDPI (0.5) | Nikalac (0.5) | A |
| Example 9 | ACDBC-4 obtained in Synthesis Example 9 (10) | PGMEA (90) | DTDPI (0.5) | Nikalac (0.5) | A |
| Example 10 | MCDBC-4 obtained in Synthesis Example 10 (10) | PGMEA (90) | DTDPI (0.5) | Nikalac (0.5) | A |
| Example 11 | AODBC mixture obtained in Synthesis Example 11 (10) | PGMEA (90) | DTDPI (0.5) | Nikalac (0.5) | A |
| Example 12 | MAODBC mixture obtained in Synthesis Example 12 (10) | PGMEA (90) | DTDPI (0.5) | Nikalac (0.5) | A |
| Example 13 | SDBC-4 obtained in Synthesis Example 13 (10) | PGMEA (90) | DTDPI (0.5) | Nikalac (0.5) | A |

TABLE 1-continued

| | Compound or Resin (parts by mass) | Organic solvent (parts by mass) | Acid generating agent (parts by mass) | Crosslinking agent (parts by mass) | Evaluation of etching resistance |
|---|---|---|---|---|---|
| Example 14 | TAODBC obtained in Synthesis Example 14 (10) | PGMEA (90) | DTDPI (0.5) | Nikalac (0.5) | A |
| Comparative Example 1 | CR-1 (10) | PGMEA (90) | DTDPI (0.5) | Nikalac (0.5) | C |

Example 15

Then, the composition for forming a film for lithography in Example 2 was coated on a SiO$_2$ substrate having a film thickness of 300 nm, and baked at 240° C. for 60 seconds and further at 400° C. for 120 seconds to thereby form an underlayer film having a film thickness of 70 nm. A resist solution for ArF was coated on the underlayer film, and baked at 130° C. for 60 seconds to thereby form a photoresist layer having a film thickness of 140 nm. As the resist solution for ArF, one prepared by blending 5 parts by mass of the compound of the following formula (11), 1 part by mass of triphenylsulfonium nonafluoromethanesulfonate, 2 parts by mass of tributylamine, and 92 parts by mass of PGMEA was used.

A compound of following formula (11) was prepared as follows. That is, 4.15 g of 2-methyl-2-methacryloyloxyadamantane, 3.00 g of methacryloyloxy-y-butyrolactone, 2.08 g of 3-hydroxy-1-adamantyl methacrylate and 0.38 g of azobisisobutyronitrile were dissolved in 80 mL of tetrahydrofuran to provide a reaction solution. This reaction solution was subjected to polymerization under a nitrogen atmosphere for 22 hours with the reaction temperature being kept at 63° C., and thereafter the reaction solution was dropped in 400 mL of n-hexane. A product resin thus obtained was solidified and purified, and a white powder produced was taken by filtration and dried under reduced pressure at 40° C. overnight to provide a compound represented by the following formula.

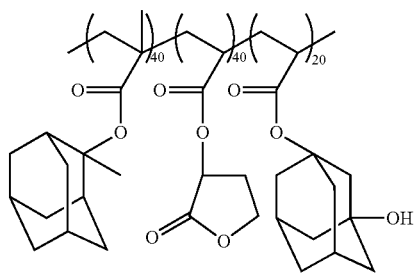

(11)

In the formula (11), the numerals 40, 40, and 20 indicate the proportions of the respective constituent units, and do not mean a block copolymer.

Then, the photoresist layer was exposed by using an electron beam lithography apparatus (ELS-7500, produced by Elionix, Inc., 50 keV), baked at 115° C. for 90 seconds (PEB), and developed with a 2.38% by mass aqueous tetramethylammonium hydroxide (TMAH) solution for 60 seconds, thereby providing a positive-type resist pattern.

Comparative Example 2

Except that no underlayer film was formed, the same manner as in Example 15 was performed to form a photoresist layer directly on a SiO$_2$ substrate to provide a positive-type resist pattern.

[Evaluation]

The shapes of the resist patterns of 55 nm L/S (1:1) and 80 nm L/S (1:1) provided in each of Example 15 and Comparative Example 2 were observed by using an electron microscope (S-4800) manufactured by Hitachi Ltd. A case where the shape of the resist pattern after development had no pattern collapse and had good rectangularity was evaluated to be good and a case the shape had pattern collapse and did not have good rectangularity was evaluated to be poor. In the observation results, the minimum line width where there was no pattern collapse and rectangularity was good was defined as the resolution and used as an evaluation index. Furthermore, the minimum amount of electron beam energy, where a good pattern shape could be drawn, was defined as the sensitivity and used as an evaluation index. The results are shown in Table 2.

TABLE 2

| | Material for forming underlayer film | Resolution (nmL/S) | Sensitivity ($\mu C/cm^2$) | Resist pattern formation after development |
|---|---|---|---|---|
| Example 15 | Material described in Example 2 | 60 | 18 | Good |
| Comparative Example 2 | Not used | 90 | 38 | Poor |

As can be seen from Table 2, it was confirmed that Example 15 was significantly excellent in resolution and sensitivity as compared with Comparative Example 2. It was also confirmed that the resist pattern shape after development had no pattern collapse and had good rectangularity. Furthermore, it was shown from the difference in the resist pattern shape after development that the material for forming a film for lithography in Example 15 had good adhesiveness with a resist material.

The material for forming a film for lithography of the present invention have a relatively high carbon concentration, a relatively low oxygen concentration, a relatively high heat resistance and also a relatively high solvent solubility, and which can be applied to a wet process. Therefore, the material for forming a film for lithography, the underlayer composition for forming a film for lithography, containing the material, and the underlayer film formed using the composition, of the present invention, can be widely and effectively utilized in various applications in which these properties are required.

The invention claimed is:

1. A composition for forming a film for lithography comprising:
    a material for forming the film for lithography comprising a resin obtained through a reaction of at least a compound represented by the following formula (1) with a compound having crosslinking reactivity

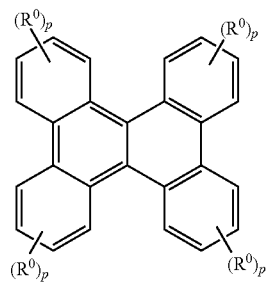

(1)

wherein, each $R^0$ independently represents a monovalent group having an oxygen atom, a monovalent group having a sulfur atom, a monovalent group having a nitrogen atom, a hydrocarbon group or a halogen atom, and each p is independently an integer of 0 to 4; and an acid generating agent.

2. The composition according to claim 1, wherein at least one p is an integer of 1 to 4.

3. The composition according to claim 1, wherein at least one $R^0$ represents the monovalent group having the oxygen atom.

4. The composition according to claim 1, wherein the compound having crosslinking reactivity is an aldehyde, a ketone, a carboxylic acid, a carboxylic acid halide, a halogen-containing compound, an amino compound, an imino compound, an isocyanate, or an unsaturated hydrocarbon group-containing compound.

5. The composition according to claim 1, wherein the resin is at least one selected from the group consisting of a novolac-based resin, an aralkyl-based resin, a hydroxystyrene-based resin, a (meth)acrylic acid-based resin and copolymers thereof.

6. The composition according to claim 1, wherein the compound represented by the formula (1) is a compound represented by the following formula (2):

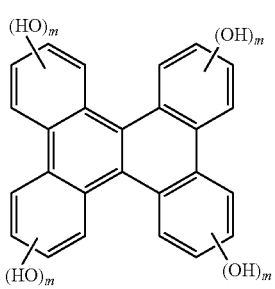

(2)

wherein, each m is independently an integer of 0 to 4, in which at least one m is an integer of 1 to 4.

7. The composition according to claim 1, wherein the resin has at least one structure selected from the group consisting of structures represented by the following formulae (3-1) to (3-16):

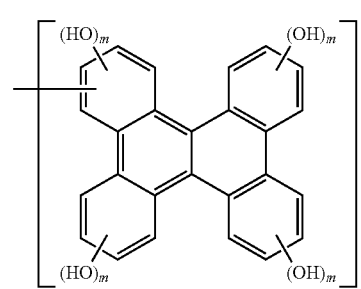

(3-1)

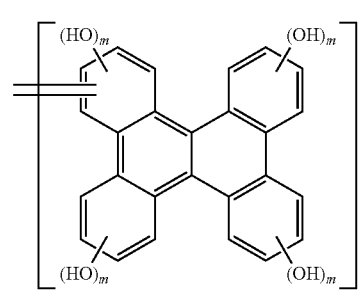

(3-2)

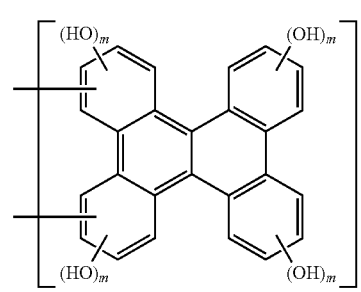

(3-3)

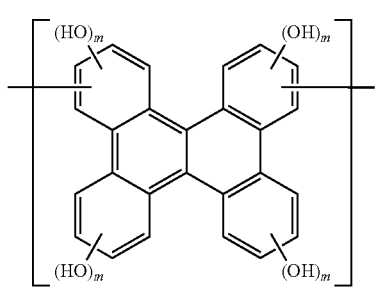

(3-4)

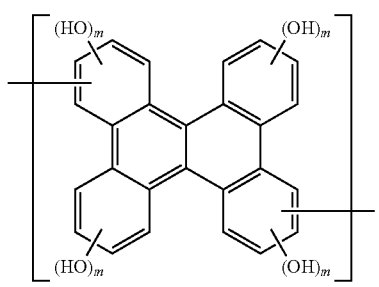

(3-5)

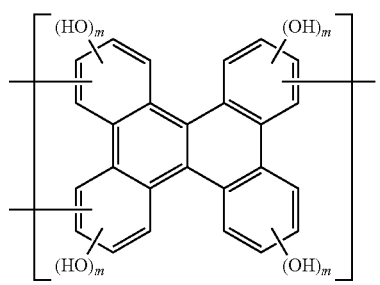
(3-6)
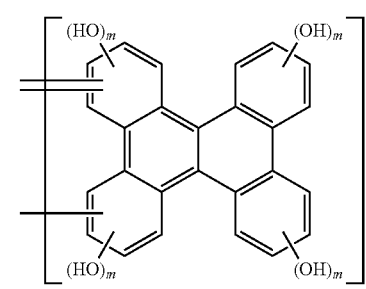
(3-7)
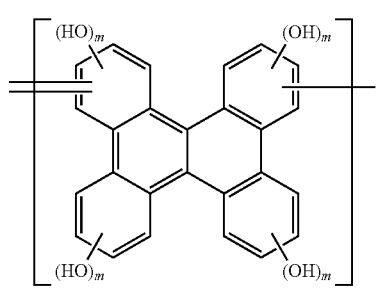
(3-8)
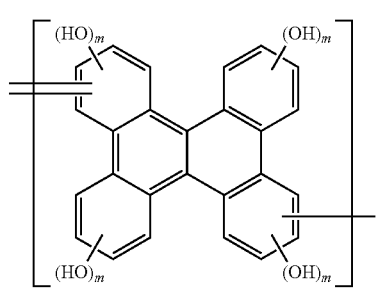
(3-9)
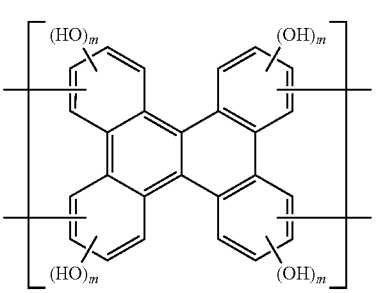
(3-10)
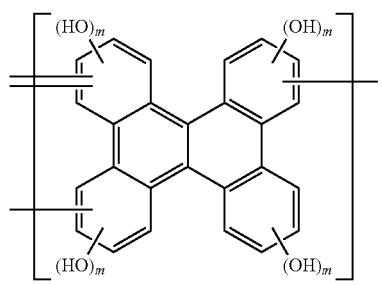
(3-11)
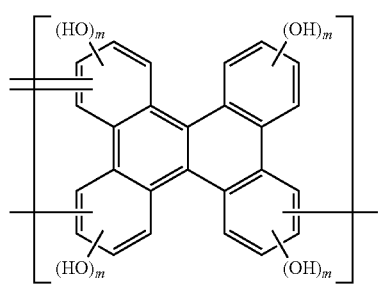
(3-12)
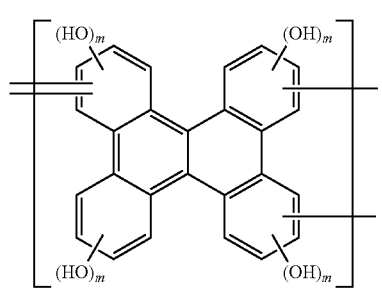
(3-13)
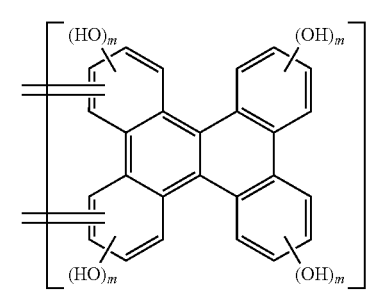
(3-14)
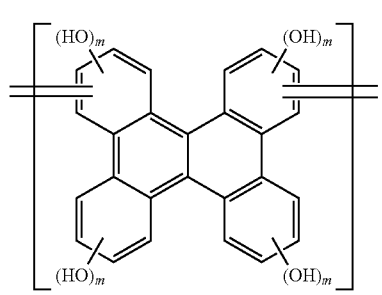
(3-15)

-continued (3-16)

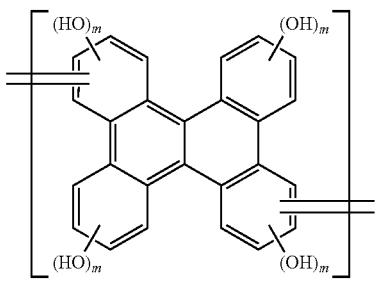

wherein, each m is independently an integer of 0 to 4, in which at least one m is an integer of 1 to 4.

8. A composition for forming a film for lithography comprising:
a material for forming a film for lithography comprising a compound represented by formula (1), (1)

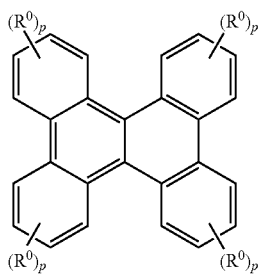

wherein, each $R^0$ independently represents a monovalent group having an oxygen atom, a monovalent group having a sulfur atom, a monovalent group having a nitrogen atom, a hydrocarbon group or a halogen atom, and each p is independently an integer of 0 to 4 with at least one p being an integer of 1 to 4;
an organic solvent; and
an acid generating agent.

9. A film for lithography, formed using a composition comprising:
a material for forming the film for lithography comprising a compound represented by formula (1), (1)

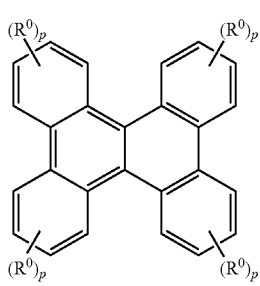

wherein, each $R^0$ independently represents a monovalent group having an oxygen atom, a monovalent group having a sulfur atom, a monovalent group having a nitrogen atom, a hydrocarbon group or a halogen atom, and each p is independently an integer of 0 to 4 with at least one p being an integer of 1 to 4;
an acid generating agent; and
an organic solvent.

10. A resist pattern forming method, comprising
step (A-1) of forming a film on a substrate by using a composition for forming the film comprising a material for forming the film for lithography comprising a compound represented by formula (1), (1)

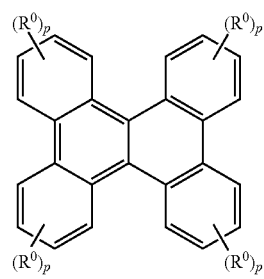

wherein, each $R^0$ independently represents a monovalent group having an oxygen atom, a monovalent group having a sulfur atom, a monovalent group having a nitrogen atom, a hydrocarbon group or a halogen atom, and each p is independently an integer of 0 to 4, and an organic solvent,
step (A-2) of forming at least one photoresist layer on the film, and
step (A-3) of, after step (A-2), irradiating a predetermined region of the photoresist layer with radiation, followed by developing.

11. A circuit pattern forming method comprising
step (B-1) of forming a film on a substrate by using a composition for forming a film for lithography, comprising an organic solvent and a compound represented by formula (1), (1)

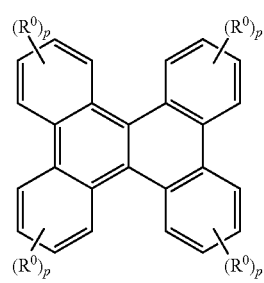

wherein, each $R^0$ independently represents a monovalent group having an oxygen atom, a monovalent group having a sulfur atom, a monovalent group having a nitrogen atom, a hydrocarbon group or a halogen atom, and each p is independently an integer of 0 to 4;
step (B-2) of forming an intermediate layer film on the film by using a silicon atom-containing resist intermediate layer film material,
step (B-3) of forming at least one photoresist layer on the intermediate layer film,
step (B-4) of, after step (B-3), irradiating a predetermined region of the photoresist layer with radiation, followed by developing to form a resist pattern, and
step (B-5) of, after step (B-4), etching the intermediate layer film with the resist pattern as a mask, etching the film with the obtained intermediate layer film pattern as an etching mask and etching the substrate with the obtained film pattern as an etching mask, to form a pattern on the substrate.

12. A method for purifying a composition for forming a film for lithography, the method comprising:
providing a material for forming the film for lithography comprising a resin obtained through a reaction of at least a compound represented by the following formula (1) with a compound having crosslinking reactivity

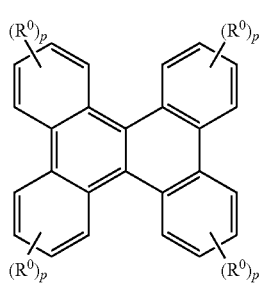

(1)

wherein, each $R^0$ independently represents a monovalent group having an oxygen atom, a monovalent group having a sulfur atom, a monovalent group having a nitrogen atom, a hydrocarbon group or a halogen atom, and each p is independently an integer of 0 to 4;
bringing a solution (A) comprising an organic solvent optionally immiscible with water, and the material for forming a film for lithography into contact with an acidic aqueous solution for extraction to form a purified material; and
combining at least one of an acid generating agent and an acid crosslinking agent with at least one of the purified material and the material for forming the film for lithography.

13. A method for forming a film for lithography comprising the steps of:
obtaining a composition for forming a film for lithography, the composition comprising a compound represented by the following formula (1):

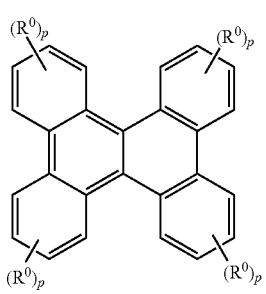

(1)

wherein, each $R^0$ independently represents a monovalent group having an oxygen atom, a monovalent group having a sulfur atom, a monovalent group having a nitrogen atom, a hydrocarbon group or a halogen atom, and each p is independently an integer of 0 to 4 with at least one p being an integer of 1 to 4; and
forming a film for lithography from the composition and an acid generating agent.

14. The method of claim 13, wherein at least one RD represents the monovalent group having the oxygen atom.

15. The method of claim 13, wherein the compound represented by the formula (1) is a compound represented by the following formula (2):

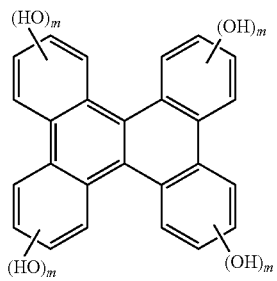

(2)

wherein, each m is independently an integer of 0 to 4, in which at least one m is an integer of 1 to 4.

16. The method of claim 15, wherein the compound represented by the formula (2) is at least one selected from the group consisting of compounds represented by the following formulae (2-1) to (2-6):

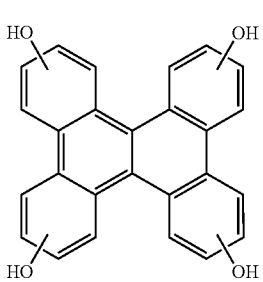

(2-1)

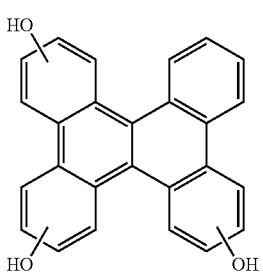

(2-2)

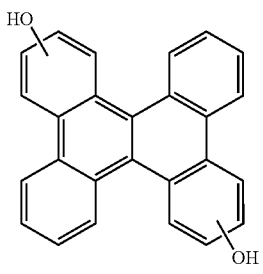

(2-3)

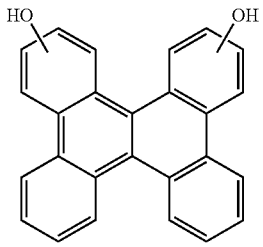

(2-4)

-continued
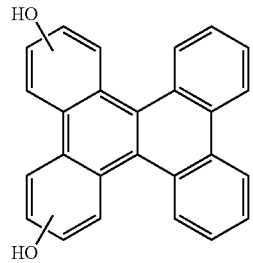
(2-5)
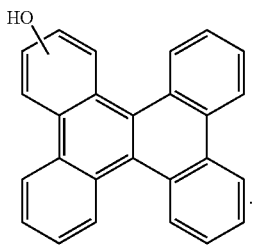
(2-6)
17. The method of claim 13, further comprising the step of combining the composition with an organic solvent.

UNITED STATES PATENT AND TRADEMARK OFFICE
CERTIFICATE OF CORRECTION

PATENT NO. : 10,310,377 B2
APPLICATION NO. : 15/309758
DATED : June 4, 2019
INVENTOR(S) : Takashi Makinoshima and Masatoshi Echigo It is certified that error appears in the above-identified patent and that said Letters Patent is hereby corrected as shown below:

In the Claims

Column 63, Line (63):
In Claim 14, please delete "RD" and insert -- $R^0$ --, therefor.

Signed and Sealed this
Twenty-fourth Day of September, 2019

Andrei Iancu
*Director of the United States Patent and Trademark Office*